US009865447B2

(12) United States Patent
Chuang et al.

(10) Patent No.: US 9,865,447 B2
(45) Date of Patent: Jan. 9, 2018

(54) HIGH BRIGHTNESS LASER-SUSTAINED PLASMA BROADBAND SOURCE

(71) Applicant: KLA-Tencor Corporation, Milpitas, CA (US)

(72) Inventors: Yung-Ho Alex Chuang, Cupertino, CA (US); Xiaoxu Lu, San Jose, CA (US); Justin Liou, Santa Clara, CA (US); John Fielden, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/285,333

(22) Filed: Oct. 4, 2016

(65) Prior Publication Data
US 2017/0278694 A1  Sep. 28, 2017

Related U.S. Application Data

(60) Provisional application No. 62/314,169, filed on Mar. 28, 2016.

(51) Int. Cl.
*H01J 61/16* (2006.01)
*H01L 21/48* (2006.01)
(Continued)

(52) U.S. Cl.
CPC ............ *H01J 61/025* (2013.01); *H01J 61/16* (2013.01); *H01J 61/20* (2013.01); *H05H 1/24* (2013.01)

(58) Field of Classification Search
CPC ............ H01L 21/485; H01L 21/76888; H01L 21/76894; H01L 22/12; G01N 21/6408; G01N 21/6428; G01N 21/6454; G01N 21/648; G02B 27/0103; G02B 5/32; H01S 3/06754; H01S 3/094042; H01S 3/094069; H01S 3/09415; H01S 3/2308; H05G 2/005; H05G 2/008
(Continued)

(56) References Cited

U.S. PATENT DOCUMENTS 4,999,014 A  3/1991  Gold et al.
5,181,080 A  1/1993  Fanton et al.
(Continued)

FOREIGN PATENT DOCUMENTS

JP          61193358 B1   8/1986
KR     1020150093858 A   8/2015

OTHER PUBLICATIONS

U.S. Appl. No. 15/280,073, filed Sep. 29, 2016, Anant Chimmalgi et al.
(Continued)

*Primary Examiner* — David A Vanore
(74) *Attorney, Agent, or Firm* — Suiter Swantz pc llo

(57) ABSTRACT

The broadband light source includes a gas containment structure and a pump laser for generating a pump beam including illumination of a wavelength near that of a weak absorption line of a neutral gas contained in the gas containment structure. The broadband light source also includes anamorphic optics for focusing the pump beam into an elliptical beam waist positioned in or near the center of the gas containment structure. The broadband light source also includes collection optics for collecting broadband radiation emitted by the plasma in a direction aligned with a longer axis of the elliptical beam waist.

38 Claims, 13 Drawing Sheets

(51) Int. Cl.
*H01J 61/02* (2006.01)
*H01J 61/20* (2006.01)
*H05H 1/24* (2006.01)

(58) Field of Classification Search
USPC .............. 250/492.2, 492.23, 504 R; 359/15; 372/6
See application file for complete search history.

(56) References Cited

U.S. PATENT DOCUMENTS

| | | | |
|---|---|---|---|
| 5,608,526 A | 3/1997 | Piwonka-Corle et al. | |
| 5,877,859 A | 3/1999 | Aspnes et al. | |
| 5,999,310 A | 12/1999 | Shafer et al. | |
| 6,288,780 B1 | 9/2001 | Fairley et al. | |
| 6,297,880 B1 | 10/2001 | Rosencwaig et al. | |
| 6,429,943 B1 | 8/2002 | Opsal et al. | |
| 6,788,404 B2 | 9/2004 | Lange | |
| 6,972,268 B2* | 12/2005 | Ehrmann | B23K 26/032 250/492.2 |
| 7,345,825 B2 | 3/2008 | Chuang et al. | |
| 7,394,476 B2* | 7/2008 | Cordingley | B23K 26/032 219/121.6 |
| 7,435,982 B2 | 10/2008 | Smith | |
| 7,525,649 B1 | 4/2009 | Leong et al. | |
| 7,705,331 B1 | 4/2010 | Kirk et al. | |
| 7,955,906 B2* | 6/2011 | Cordingley | B23K 26/032 219/121.6 |
| 7,957,066 B2 | 6/2011 | Armstrong et al. | |
| 8,259,771 B1 | 9/2012 | Shchemelinin et al. | |
| 8,517,585 B1 | 8/2013 | Bezel et al. | |
| 8,618,254 B2 | 12/2013 | Giaccia et al. | |
| 8,809,734 B2* | 8/2014 | Cordingley | B23K 26/032 219/121.76 |
| 8,921,814 B2 | 12/2014 | Pellemans et al. | |
| 9,678,012 B2* | 6/2017 | Rothberg | G01N 21/6408 |
| 2003/0063629 A1* | 4/2003 | Davis | H01S 3/063 372/6 |
| 2004/0066547 A1* | 4/2004 | Parker | G02B 5/32 359/15 |
| 2004/0264512 A1 | 12/2004 | Hartlove et al. | |
| 2005/0167618 A1 | 8/2005 | Hoshino et al. | |
| 2007/0228300 A1 | 10/2007 | Smith | |
| 2011/0291566 A1 | 12/2011 | Bezel et al. | |
| 2013/0001438 A1 | 1/2013 | Bezel et al. | |
| 2013/0017205 A1 | 1/2013 | Giaccia et al. | |
| 2013/0342105 A1 | 12/2013 | Shchemelinin et al. | |
| 2015/0163893 A1 | 6/2015 | Park et al. | |
| 2015/0208494 A1 | 7/2015 | Rafac et al. | |
| 2015/0282288 A1 | 10/2015 | Bezel et al. | |
| 2016/0005588 A1 | 1/2016 | Park et al. | |
| 2017/0052456 A1* | 2/2017 | Van Schoot | G03F 7/70033 |

OTHER PUBLICATIONS

U.S. Appl. No. 15/274,956, filed Sep. 23, 2016, Anant Chimmalgi et al.

Wilbers et al., The VUV Emissivity of a High-Pressure Cascade Argon Arc from 125 to 200 nm, J. Quant. Spectrosc. Radiat. Transfer, vol. 46, Jan. 1991, pp. 299-308, Printed in Great Britain. Pergamon Press.

Wilbers et al., The Continuum Emission of Arc Plasma, J. Quant. Spectrosc. Radiat. Transfer, vol. 45, No. 1, 1991, pp. 1-10.

G. Beck, Simple Pulse Generator for Pulsing Xenon Arcs with High Repetition Rage, Rev. Sci. Instrum., vol. 45, No. 2, Feb. 1974, pp. 318-319.

Raizer, Optical Discharges, Sov. Phys. Usp. vol. 23, No. 11, Nov. 1980, pp. 789-806.

Fiedorowicz et al., X-Ray Emission from Laser-Irradiated Gas Puff Targets, Appl. Phys. Lett., vol. 62, Issue 22, May 31, 1993, pp. 2778-2780.

Keefer et al., Experimental Study of a Stationary Laser-Sustained Air Plasma, Journal of Applied Physics, vol. 46, No. 3, Mar. 1975, pp. 1080-1083.

Jeng et al., Theoretical Investigation of Laser-Sustained Argon Plasmas, J. Appl. Phys. vol. 60, No. 7, Oct. 1, 1986, pp. 2272-2279.

Carlton D. Moody, Maintenance of a gas breakdown in argon using 10.6-µ cw radiation, Journal of Applied Physics, vol. 46, No. 6, Jun. 1975, pp. 2475-2482.

Douglas L. Franzen, CW Gas Breakdown in Argon Using 10.6-µm Laser Radiation, Appl. Phys. Lett., vol. 21, No. 2, Jul. 15, 1972, pp. 62-64.

Carlhoff et al., Continuous Optical Discharges at Very High Pressure, Physica, vol. 103, Issues 2-3, Feb. 1981, pp. 439-447.

Cremers et al., Evaluation of the Continuous Optical Discharge for Spectrochemical Analysis, Spectrochimica Acta, vol. 40, No. 4, 1985, pp. 665-679, Printed in Great Britain, Pergamon Press Ltd.

Hamamatsu Product Information, Super-Quiet Xenon Lamp Super-Quiet Mercury-Xenon Lamp, Nov. 2005, 16 pages, Printed online at: https://www.hamamatsu.com/resources/pdf/etd/Xe-HgXe_TLSX1044E.pdf.

G.I. Kozlov et al., Radiative losses by argon plasma and the emissive model of a continuous optical discharge, Sov. Phys. JETP, vol. 39, No. 3, Sep. 1974, pp. 463-468.

Fanton et al., Multiparameter measurements of thin films using beam-profile reflectivity, Journal of Applied Physics, vol. 73, No. 11, pp. 7035-7040, Jun. 1, 1993.

J.M. Leng et al., Simultaneous measurement of six layers in a silicon on insulator film stack using spectrophotometry and beam profile reflectometry, Journal of Applied Physics, vol. 81, No. 8, Apr. 15, 1997, pp. 3570-358.

* cited by examiner

HIGH BRIGHTNESS LASER-SUSTAINED PLASMA BROADBAND SOURCE

CROSS-REFERENCE TO RELATED APPLICATION

The present application claims the benefit under 35 U.S.C. §119(e) of U.S. Provisional Application Ser. No. 62/314,169, filed Mar. 28, 2016, entitled LASER-PUMPED PLASMA LAMPS WITH HIGHER BRIGHTNESS, naming Yung-Ho Alex Chuang, Xiaoxu Lu, Justin Liou and John Fielden as inventors, which is incorporated herein by reference in the entirety.

TECHNICAL FIELD

The present invention generally relates to plasma-based light sources, and, more particularly, to high brightness plasma-based broadband light sources for use in inspection or metrology systems.

BACKGROUND

The need for improved illumination sources used for characterization of ever-shrinking integrated circuit device features continues to grow. Semiconductor metrology and inspection systems require very stable, very bright (high radiance) broadband light sources to perform precise measurements of small dimensions and/or detect small defects. Increasing the brightness of light sources creates higher throughput and higher sensitivity.

In previous approaches, Xe, Ag or Hg arc lamps have been used to produce broadband light. The arc lamps include an anode and cathode, which generate an electric discharge to excite and ionize the gas and sustain it at a high temperature, while broadband light is emitted from the excited and ionized gas. During operation, the anode and the cathode become very hot, and are prone to wear by evaporation and sputtering of material from their surfaces. Material lost from the electrodes can contaminate the gas and envelope and reduce its light output (particularly at UV wavelengths, where even a very thin layer of material deposited on the lamp envelope or window can substantially reduce UV transmission) or result in failure of the light source. More importantly, these arc lamps do not provide sufficient brightness (spectral radiance) for some applications, including inspection and metrology applications within the semiconductor and related industries. The brightness of arc lamps is limited by the attainable current density, which in turn is limited, in part, by the need to avoid excessive wear of the electrodes and an uneconomically short lamp lifetime.

Spectral radiance, or brightness (i.e., the emitted light power per unit area per unit solid angle per unit wavelength), is very important for light sources intended for use in semiconductor inspection and metrology systems. Such systems typically illuminate a relatively small area at any one time (such as an area with dimensions between a few microns and a few hundred microns). The light used to inspect or measure a sample needs to be focused into this small area on the sample with sufficient power to produce enough reflected and/or scattered light to create a signal with a high signal-to-noise ratio. Since an optical system comprising lenses, mirrors etc. can, at best, only preserve spectral radiance (if completely lossless), a high spectral radiance is required from the light source to deliver a high power into a small area. It is noted that, at best, simply increasing the power and size of the plasma of a plasma lamp will provide an inefficient means to increase the amount of power delivered to a given area, and, at worst, may not increase the power that can be delivered to the given area at all.

Arc lamps simply lack sufficient brightness for critical inspection and metrology applications in the semiconductor industry. The lifetime is limited due to the hot temperature of the electrodes. Furthermore, the position of the arc can be unstable.

In some inspection and metrology systems, a laser-sustained (LSP) plasma lamp has been implemented. A LSP lamp can be brighter than an arc lamp, emit over a larger spectral range and have a much longer lifetime. A LSP lamp may comprise a transparent envelope (such as an envelope made from fused silica) with two electrodes and filled with pressurized gas similar to a conventional arc lamp. A laser beam at an infra-red (IR) wavelength may be focused to the center of the plasma. A brief electrical discharge is created between the electrodes by applying a high voltage to ignite a plasma and hot gas where the laser is focused. The laser energy absorbed by the plasma and hot gas is used to sustain the plasma after the voltage between the electrodes is turned off. The tightly focused laser can generate a plasma size as small as 100 microns and a plasma temperature between 10,000K and 20,000K. Because of the small size and high temperature of the plasma compared with a conventional arc lamp (which typically has an arc length of a few mm), LSP light sources are much brighter and emit more light with short wavelengths. Since an electrical discharge between the electrodes exists only briefly to start the lamp, wear of the electrodes is dramatically reduced or made negligible, greatly increasing the lamp life compared with a conventional arc lamp. Furthermore, the size of the plasma is a better match to the source size required by typical semiconductor inspection and metrology systems so that the collection efficiency can be higher compared to a conventional arc lamp.

While LSP lamps are brighter than the arc lamps, in order to meet the demand for inspecting/measuring ever smaller defects, existing LSP light sources are insufficient. Simply increasing the laser pump power merely increases the size of the plasma and the surrounding hot gas, while the center of the plasma does not become significantly hotter. This occurs because the most of the laser pump light power is absorbed by the hot, but largely unionized gas, surrounding the plasma, resulting in little of the increased pump power reaching the plasma core. As a result, the brightness of a LSP plasma source tends to saturate at high pump powers. In addition, as the pump laser power increases, the plasma can become unstable.

Therefore, it would be desirable to provide a broadband source that cures the various shortcomings of prior approaches, such as those described above.

SUMMARY

A high brightness laser-sustained plasma broadband light source is disclosed, in accordance with one or more embodiments of the present disclosure. In one embodiment, the light source includes a gas containment structure. In another embodiment, the light source includes a pump laser configured to generate a pump beam including illumination of a wavelength at least proximate to a weak absorption line of a neutral gas contained in the gas containment structure. In another embodiment, the light source includes one or more anamorphic illumination optics configured to focus the pump beam into an approximately elliptical beam waist positioned in or proximate to the center of the gas containment structure. In another embodiment, the light source includes one or more first collection optics configured to collect broadband radiation emitted by the plasma in a direction substantially aligned with a longer axis of the elliptical beam waist.

A method to generate high brightness broadband light is disclosed, in accordance with one or more embodiments of the present disclosure. In one embodiment, the method includes providing a volume of gas in a gas containment structure. In another embodiment, the method includes igniting a plasma within the volume of the gas in the gas containment structure. In another embodiment, the method includes generating a pump laser beam including illumination having a wavelength at least proximate to a weak neutral absorption line of the gas in the gas containment structure. In another embodiment, the method includes shaping and focusing the pump laser beam with one or more anamorphic illumination optics to form an elliptical beam waist located at least proximate to the center of the gas containment structure. In another embodiment, the method includes collecting broadband radiation emitted by the plasma in a direction substantially aligned with a longer axis of the elliptical beam waist.

It is to be understood that both the foregoing general description and the following detailed description are exemplary and explanatory only and are not necessarily restrictive of the present disclosure. The accompanying drawings, which are incorporated in and constitute a part of the characteristic, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Figure 1A:
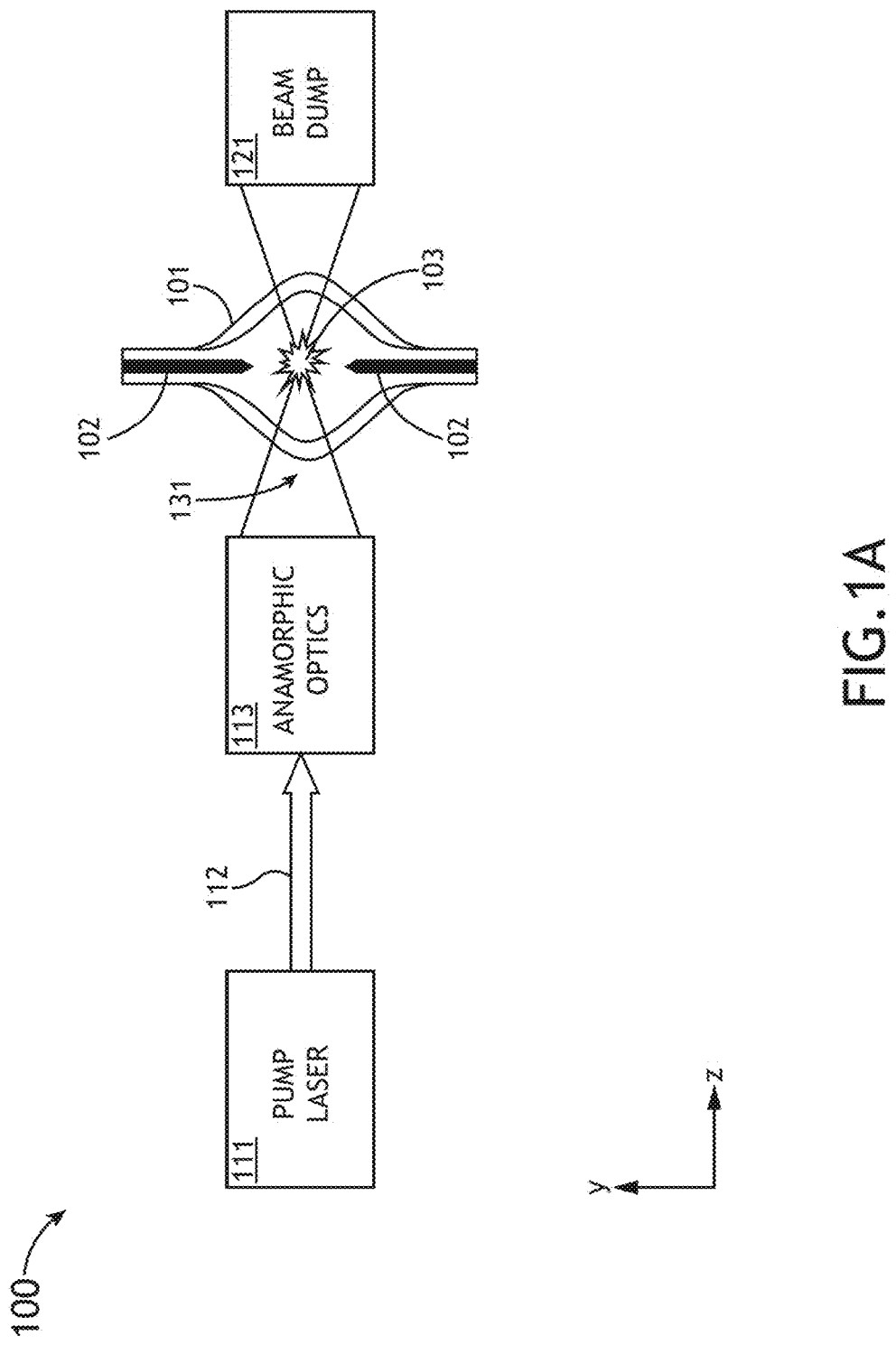
FIGS. 1A-1B illustrate a simplified schematic view of a system for generating high brightness LSP broadband radiation, in accordance with one or more embodiments of the present disclosure.

Reference will now be made in detail to the subject matter disclosed, which is illustrated in the accompanying drawings.

Referring generally to FIGS. 1A through 7, a high brightness laser-sustained plasma (LSP) source is described, in accordance with one or more embodiments of the present disclosure.

Embodiments of the present disclosure are directed to the generation of a high brightness plasma in a laser-sustained broadband radiation source, so the performance of associated metrology and/or inspection systems may be improved. Embodiments of the present disclosure are directed to a laser-sustained plasma source that creates a high temperature plasma that is well controlled in its dimensions even with normal variations in laser characteristics such as, but not limited to, $M^2$ and an envelope shape, and has a high optical density (i.e., opacity) in the direction in which the output light is directed.

Embodiments of the present disclosure are directed to focusing a pump beam to a sharp, but elongated image with high NA in the tightly-focused direction and the collection of the radiation along the elongated direction. Such a focusing configuration provides for the increase in the pump volume and collection depth without increasing the plasma size in the collection plane, while high pump NA helps reduce the plasma size in the tightly-focused direction and the pump beam propagation direction, so the collected radiation within the same etendue is greatly increased. Additional embodiments of the present disclosure are directed to enhancing plasma brightness by reflecting and focusing uncollected plasma radiation or leftover pump power back into the plasma. Additional embodiments of the present disclosure are directed to additional collection/reflector elements so as to increase the solid angle with which broadband radiation and/or left over pump is collected, resulting in an increase in pumping efficiency.

It is noted that a plasma source with improved brightness is especially advantageous in shorter wavelength regimes (e.g., wavelengths shorter than about 350 nm) or longer IR wavelength regimes (e.g., wavelengths longer than 1700 nm), where the intensity is historically low in previous approaches. Short UV wavelengths can be very important in inspection and metrology instruments, such as those used in the semiconductor industry, because such wavelengths are more strongly scattered by small features than longer wavelengths. In addition, more contrast may be present in such systems between different materials on the sample because some materials (e.g., silicon) are strongly absorbing at such short UV wavelengths, while other materials (e.g., silicon dioxide) may be transparent over much of the UV spectrum.

The longer IR wavelengths can also be very important in inspection and metrology instruments such as those used to inspect or measure characteristics in very deep structures, where the longer wavelength are mostly absorbed. A light source with higher radiance (brightness) at these wavelengths can enable faster, or more sensitive, measurements or inspection of small features.

Embodiments of the present disclosure utilize anamorphic optics for bidirectionally focusing pump laser light. The implementation of anamorphic optics allows the length of the long axis of the plasma to be easily optimized independently of the focusing of the short axis of the plasma. The use of focusing for the long axis also ensures that variations in $M^2$ of the pump laser beam have, at most, only a minor effect on the length of the long axis of the plasma. Light sources described herein may include additional improvements such as the use of optics to correct for aberrations caused by a gas containment structure, such as a bulb, and the use of optics to modify the Gaussian profile of the pump laser in the direction corresponding to the long axis of the plasma to produce a more uniform plasma temperature.

A laser-sustained light source is described in U.S. Pat. No. 7,435,982; U.S. Patent Publication No. 2005/0167618; U.S. Patent Publication No. 2007/0228300; U.S. Pat. No. 7,705,331; U.S. Patent Publication No. 2011/0291566; U.S. Patent Publication No. 2013/0001438; U.S. Pat. No. 8,517,585; U.S. Pat. No. 8,259,771; U.S. Pat. No. 8,921,814; and U.S. Patent Publication No. 2015/0282288, which are each incorporated herein by reference in the entirety.

Figure 1B:
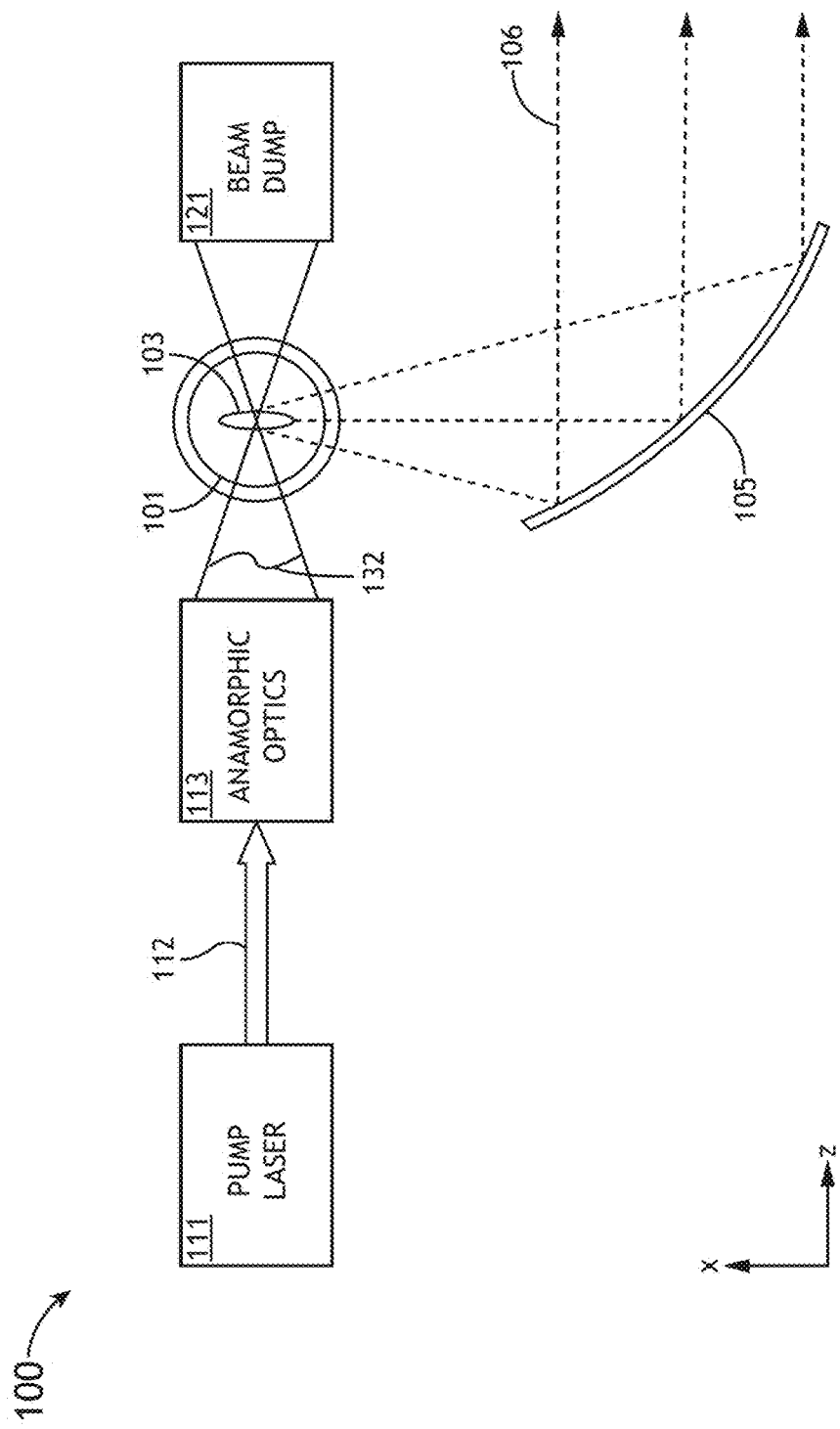

FIGS. 1A-1B illustrate a simplified schematic view of a high brightness LSP broadband radiation source 100, in accordance with one or more embodiments of the present disclosure. FIG. 1A illustrates the source 100 in the projection of the y-z plane, while FIG. 1B illustrates the source 100 in the projection of the x-z plane.

It is noted that the coordinate system illustrated herein is provided merely for illustrative and explanatory purposes. For the purposes of the present disclosure, the z-axis is defined as the pump beam propagation direction, the y-axis is aligned with the electrodes or mounting fixture of the gas containment structure/bulb and the x-axis generally corresponds to the direction of broadband radiation collection. It is noted that the various embodiments of the present disclosure can be constructed or mounted with these axes in any orientation that is convenient for its specific application.

In one embodiment, the source 100 includes a gas containment structure 101. The gas containment structure 101 may include any containment structure known in the art capable of containing a gas suitable for the formation of plasma via laser pumping. For example, the gas containment structure 101 may include, but is not limited to, a bulb, a chamber, a tube or a cell. While much of the present disclosure focuses on the implementation of a bulb as a gas containment structure 101 of source 100, it is noted that the various embodiments of the present disclosure may be extended to any gas containment structure 101.

In one embodiment, the gas used to ignite and/or sustain plasma 103 may include an inert gas (e.g., noble gas or non-noble gas) or a non-inert gas (e.g., mercury). In another embodiment, the gas used to ignite and/or sustain plasma 103 may include a mixture of gases (e.g., mixture of inert gases, mixture of inert gas with non-inert gas or a mixture of non-inert gases). For example, gases suitable for use in the gas containment structure 101 of source 100 may include, but are not limited to, Xe, Ar, Ne, Kr, He, $N_2$, $H_2O$, $O_2$, $H_2$, $D_2$, $F_2$, $CH_4$, one or more metal halides, a halogen, Hg, Cd, Zn, Sn, Ga, Fe, Li, Na, ArXe, ArHg, KrHg, XeHg, and any mixture thereof. It is further noted that a particular gas mixture may be selected so as to optimize the absorption or emission by the gas mixture. The present disclosure should be interpreted to extend to any type of gas suitable for sustaining plasma within a gas containment structure.

In another embodiment, source 100 includes a pump laser 111 configured to generate a pump beam 112 including illumination having a wavelength that is at or near (i.e., at least proximate to) a weak absorption line of a neutral gas contained in the gas containment structure 101. A weak absorption line may be a line that transitions from an excited state with an energy level more than 1 eV above the first excited state of the neutral atom to a higher energy level. For example, the first excited state of Xe is approximately 8.3 eV in energy above ground state. At plasma temperatures that are particularly useful for generating light at wavelengths between about 120 nm and about 3 μm (i.e. plasma temperatures between about 10,000 K and about 25,000 K), transitions between an excited state corresponding to an energy level more than 9.3 eV (preferably more than 9.5 eV) above ground state and higher states have relatively weak absorption because a relatively small fraction of the neutral gas away from the central region of the plasma 103 is in this higher energy excited state. In one embodiment, the pump laser 111 includes one or more continuous wave (CW) lasers, such as, but not limited to, a fiber laser or solid-state laser operating in CW mode with a wavelength close to a weak neutral absorption line (e.g., ~1070 nm) of the gas contained in the gas containment structure 101. For example, in the case of a fiber laser, the pump laser 111 may include, but is not limited to, one or more of a ytterbium (Yb)-doped fiber laser, a neodymium-doped yttrium aluminum garnet (Nd:YAG) crystal fiber laser, a neodymium-doped yttrium orthovanadate (Nd:YVO4) crystal fiber laser, neodymium-doped gadolinium vanadate (Nd:GdVO4) crystal fiber laser. By way of another example, in the case of a solid-state laser, the pump laser 111 may include, but is not limited to, one or more diode lasers.

In another embodiment, the source 100 includes one or more additional pump lasers. The one or more additional pump lasers may be arranged along a direction different than the first pump laser 111. Alternatively, the one or more additional pump lasers may be arranged in-line with the first pump laser 111 so as to impinge the gas containment structure 101 from the same direction as the first pump laser 111.

In one embodiment, the one or more additional lasers may include a green laser. For example, the one or more additional lasers may emit laser radiation with a wavelength between 515 nm and 540 nm and may be used in addition to an infrared first pump laser 111. It is noted that green light may be weakly absorbed by neutral gas (even if hot), but may be more strongly absorbed by ions, and so will mostly be absorbed by the plasma 103. It is noted that dichroic coated elements (e.g., dichroic mirrors) and/or dual-wavelength coated elements may be used to combine two lasers into one path. The combination of beams from multiple laser sources is described in U.S. application Ser. No. 15/280,073, filed on Sep. 29, 2016; and U.S. application Ser. No. 15/274,956, filed on Sep. 23, 2016, which are each incorporated herein by reference in the entirety.

In another embodiment, the source 100 includes a plasma ignition device. The plasma ignition device may create an excited an ionized gas prior to pumping by the pump laser 112. As shown in FIG. 1A, the plasma ignition device may include, but is not limited to, one or more electrodes 102. In this example, the one or more electrodes 102 may be arranged vertically (e.g., along the y-direction) to ignite the plasma 103 by causing an a.c. discharged into the gas contained in the gas containment structure 101. In another embodiment, the source 100 includes a plasma ignition laser. For example, a pulsed laser, such as, but not limited to, a Q-switched laser may illumination the gas contained within the gas containment 101 structure with a short series of high-peak power pulses, which causes ignition of the plasma 103. Plasma ignition via a pulsed laser is described in in U.S. application Ser. No. 15/280,073, filed on Sep. 29, 2016, which is incorporated above by reference in the entirety.

In another embodiment, the source 100 includes one or more beam dumps 121 positioned to capture any portion of the pump beam 112 (or additional pump beam from additional pump laser) that is not absorbed by the plasma 103.

In another embodiment, the source 100 includes one or more anamorphic illumination optics 113. For example, the one or more anamorphic illumination optics 113 may include, but are not limited to, an acylindrical lens or an aspheric lens. In one embodiment, the pump beam 112 emitted by the pump laser 111 is shaped by the one or more anamorphic illumination optics 113 and then focused to the center portion of the gas containment structure 101 to sustain the plasma 103.

In one embodiment, the one or more anamorphic illumination optics 113 are arranged to focus with a selected numerical aperture (NA) in the direction corresponding to the shorter axis (e.g., minor axis) of the elliptical beam waist, while focusing with a lower NA than the selected NA in the direction corresponding to the longer axis (e.g., major axis) of the elliptical beam waist. In one embodiment, the pump beam 112 having an wavelength at or near a weak neutral absorption line of the gas contained in the gas containment structure 101 is focused by the anamorphic illumination optics 113 to form an approximately elliptical beam waist located in or proximate to the center of the gas containment structure 101. In another embodiment, the elliptical beam waist may have a ratio of major axis to minor of at least 10. In another embodiment, the one or more anamorphic illumination optics 113 focus the pump beam 112, with a numerical aperture (NA) greater than 0.5, in the direction corresponding to the shorter axis of the elliptical beam waist to minimize the plasma size in both the direction corresponding to the shorter axis of the elliptical beam waist and the pump beam 112 propagation direction. Further, the one or more anamorphic illumination optics 113 may focus with an NA less than 0.2 in the direction corresponding to the longer axis of the elliptical beam waist to make an elongated plasma image.

In another embodiment, the one or more anamorphic illumination optics 113 are configured such that the resulting elliptical beam waist has a selected ratio of major axis to minor axis. For example, the one or more anamorphic illumination optics 113 may be configured such that the resulting elliptical beam waist has a selected ratio of major axis to minor axis of at least 10. In one embodiment, the anamorphic illumination optics 113 are configured such that elliptical beam waist has a ratio of major axis to minor of at least 10, where the minor axis of the elliptical beam waist is less than 5 μm and the major axis of the elliptical beam waist is between 50 μm and 500 μm. Furthermore, the waist size in the major axis of the elliptical beam waist may be optimized for higher brightness at the most critical wavelengths for a specific application based on the available pump power.

For example, the one or more anamorphic illumination optics 113 may focus with an NA greater than 0.5 in the y-direction corresponding to the minor axis of the elliptical beam waist (shown as 131 in FIG. 1A), while focusing with an NA less than 0.2 in the x-direction corresponding to the major axis of the elliptical beam waist (shown as 132 in FIG. 1B). In this regard, the resulting plasma 103 may have a minimized size in the y- and z-directions and an elongated shape in the x-direction (shown as 103 in FIG. 1B).

It is noted that the high NA (i.e. large pump solid angle) aids in reducing the plasma size in the tightly focused direction and the pump beam 112 propagation direction. At higher NAs, the pump intensity diverges faster around the waist location, so that the sustainability threshold for laser power density is located closer to the focus position, which results in a smaller plasma 103. Focusing the pump beam 112 to a smaller spot may also decrease the plasma size. As such, it is preferred that the pump beam 112 has good beam quality (i.e. $M^2$ close to 1.0) so it can be focused to a smaller spot and the pump beam 112 aberration at the focus is minimized with the appropriate anamorphic illumination optics 113. Without aberration, higher NA leads to smaller beam size. Because of the benefits of good pump beam 112 quality, fiber and solid-state lasers may be beneficially used in embodiments of the present disclosure.

In one embodiment, the one or more anamorphic illumination optics 113 may include one or more optical elements (e.g., lenses) that distort the Gaussian profile of the pump beam 112 in the direction of the longer axis of the focused image (e.g., by introducing a controlled amount of spherical aberration), so that the central part of the profile is flatter than a Gaussian in order to achieve a more uniform plasma temperature.

Referring to FIG. 1B, in one embodiment, the source 100 includes one or more first collection optics 105. In one embodiment, the one or more first collection optics 105 are configured to collect broadband radiation emitted by the plasma 103. For example, as shown in FIG. 1B, the one or more first collection optics 105 are configured to collect the broadband radiation from the plasma 103 in a direction substantially aligned with a longer axis of the elliptical beam waist (e.g., x-direction in which the plasma 103 is elongated). In this manner, the depth of the plasma 103 with the radiation may be collected by the one or more first collection optics 105 is larger compared with collecting the radiation from any other direction (i.e. the opacity of the plasma 103 is greatest in the collection direction). In one embodiment, the one or more first collection optics 105 include a mirror coated for high reflectively over a broadband spectral range. For example, the one or more first collection optics 105 may include, but are not limited to, a parabolic mirror, a spherical mirror or an ellipsoidal mirror. It is noted that the one or more first collection optics 105 are not limited to the examples listed above or the configuration depicted in FIG. 1B. Rather, the one or more first collection optics 105 may include any combination of reflective, refractive, and/or diffractive optics known in the art suitable for collecting broadband radiation from the plasma 103.

It is noted that source 100 may include any number and type of additional optical elements. In one embodiment, the source 100 may include one or more additional optical elements arranged to direct illumination from the one or more first collection optics 105 to one or more downstream optics, such as illuminator optics for an inspection tool or metrology tool (e.g., see FIGS. 5-7). For example, the source 100 may include one or more additional mirrors, lenses, apertures, bandwidth selective filters, and/or polarizing components (and the like) for directing and/or condition broadband radiation emitted by plasma 103.

Figure 1C:
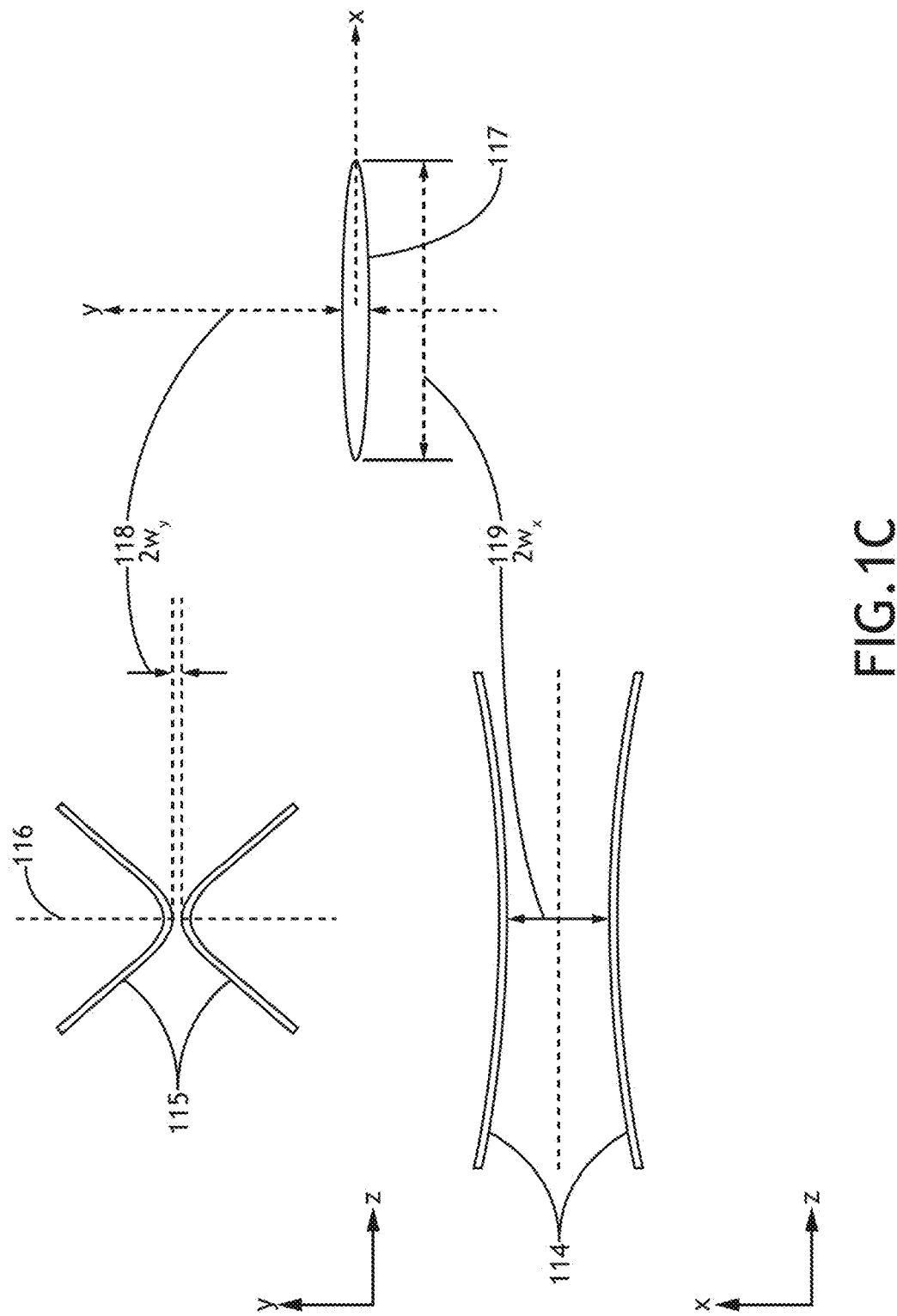
FIG. 1C illustrates a conceptual view of the beam size change of the pump beam of the system for generating high brightness LSP broadband radiation, in accordance with one or more embodiments of the present disclosure.

FIG. 1C illustrates a conceptual view of the beam size change of the pump beam 112 in both x- and y-directions along the propagation direction (z) after condition by anamorphic illumination optics 113, in accordance with one or more embodiments of the present disclosure. It is noted that caption 114 represents the pump beam 112 in the x-direction and caption 115 represents the pump beam 112 in the y-direction. In this example, the waist position 116 is well aligned with respect to each other, and is located in or proximate to the center of the gas containment structure 101. The cross-section of the elliptical beam waist is shown as 117. Caption 118 represents the waist diameter $2w_y$ in y-direction (i.e., the minor axis of the elliptical beam waist) and caption 119 represents the waist diameter $2w_x$ in x-direction (i.e., the major axis of the elliptical beam waist). For example, the anamorphic illumination optics 113 may be configured such that $2w_y$ is less than 5 μm, while $2w_x$ is between 50 μm and 500 μm, which may be further optimized based on the available pump power. It is noted that, since the pump beam 112 size and resulting Rayleigh range is very large in the x-direction, the tolerance on the waist position may be relaxed in the x-direction relative to the y-direction.

The temperature and opacity of the hot plasma 103 are two important factors determining the radiance of the light collected from the plasma 103. By focusing the light very tightly to a small beam waist in a direction (the y direction) substantially perpendicular to the direction of collection of the light output ensures that the laser pump energy is efficiently used to heat the core of the plasma 103 to high temperature. By focusing the light to a larger beam waist in a direction (the x direction) substantially parallel to the direction of collection of the light output, the opacity in this direction is increased. Since opacity depends on the number of hot and ionized atoms along the line of sight, increasing the fill pressure of the lamp can further increase the opacity. Traditional short-arc Xe arc lamps may use a fill pressure at room temperature of approximately 30 atmospheres. In one embodiment the anamorphic illumination optics 113 are used in combination with a bulb, chamber, cell or tube with a room-temperature fill pressure of about 40 atmospheres or higher so as to further increase the radiance of the collected output light.

Figure 2A:
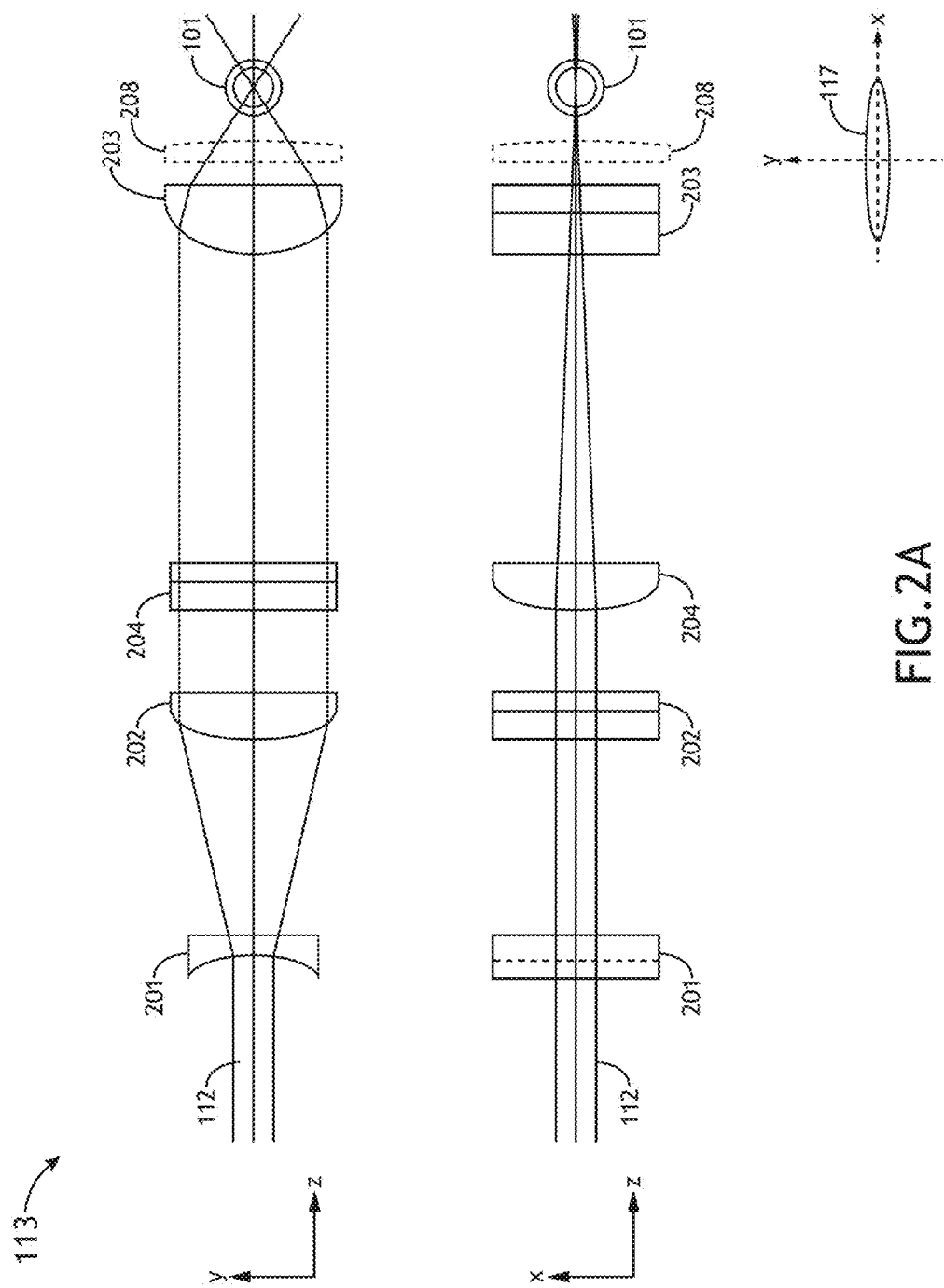
FIGS. 2A-2C illustrate schematic views of a set of anamorphic optics suitable for implementation in the system for generating high brightness LSP broadband radiation, in accordance with one or more embodiments of the present disclosure.
Figure 2B:
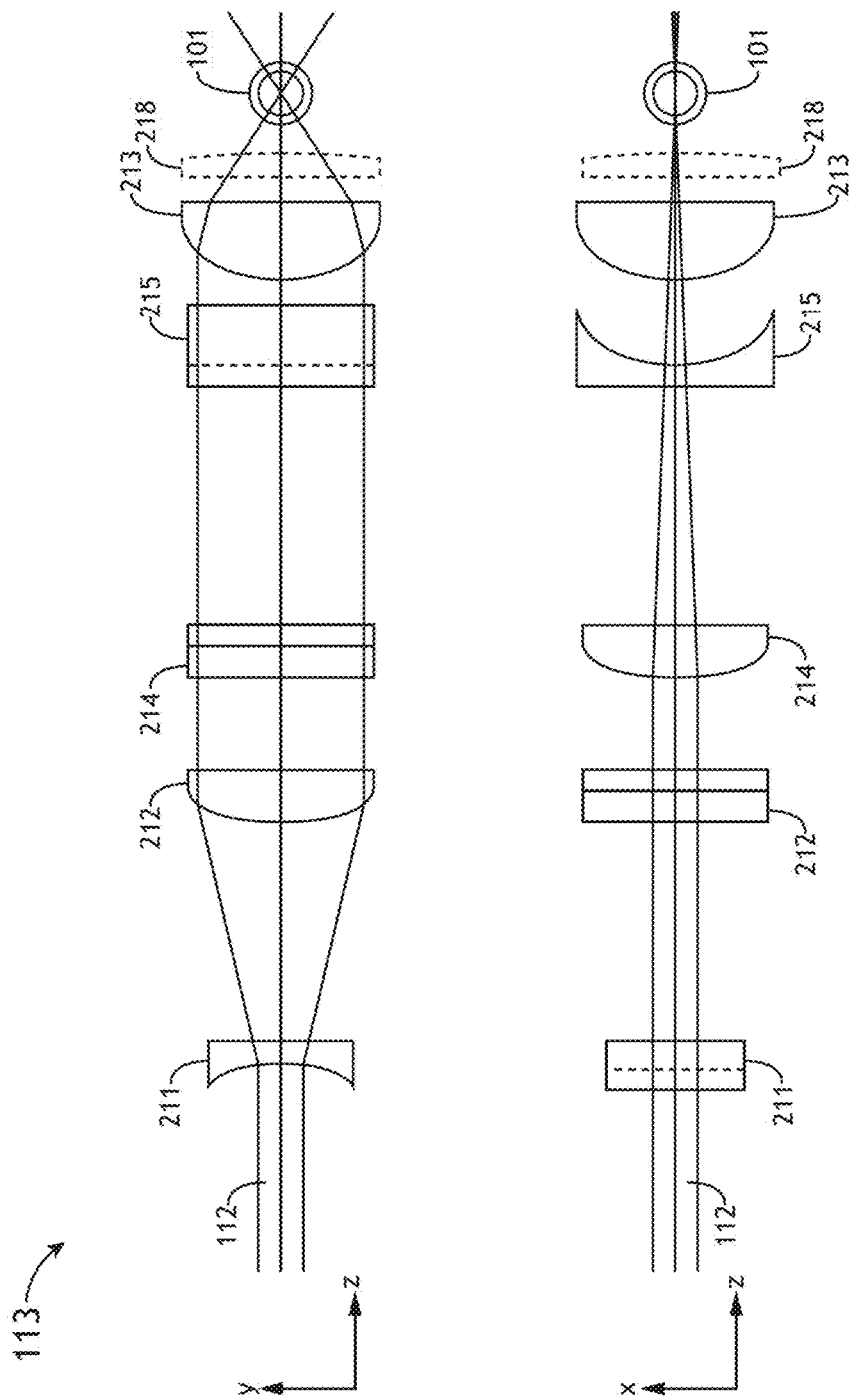
Figure 2C:
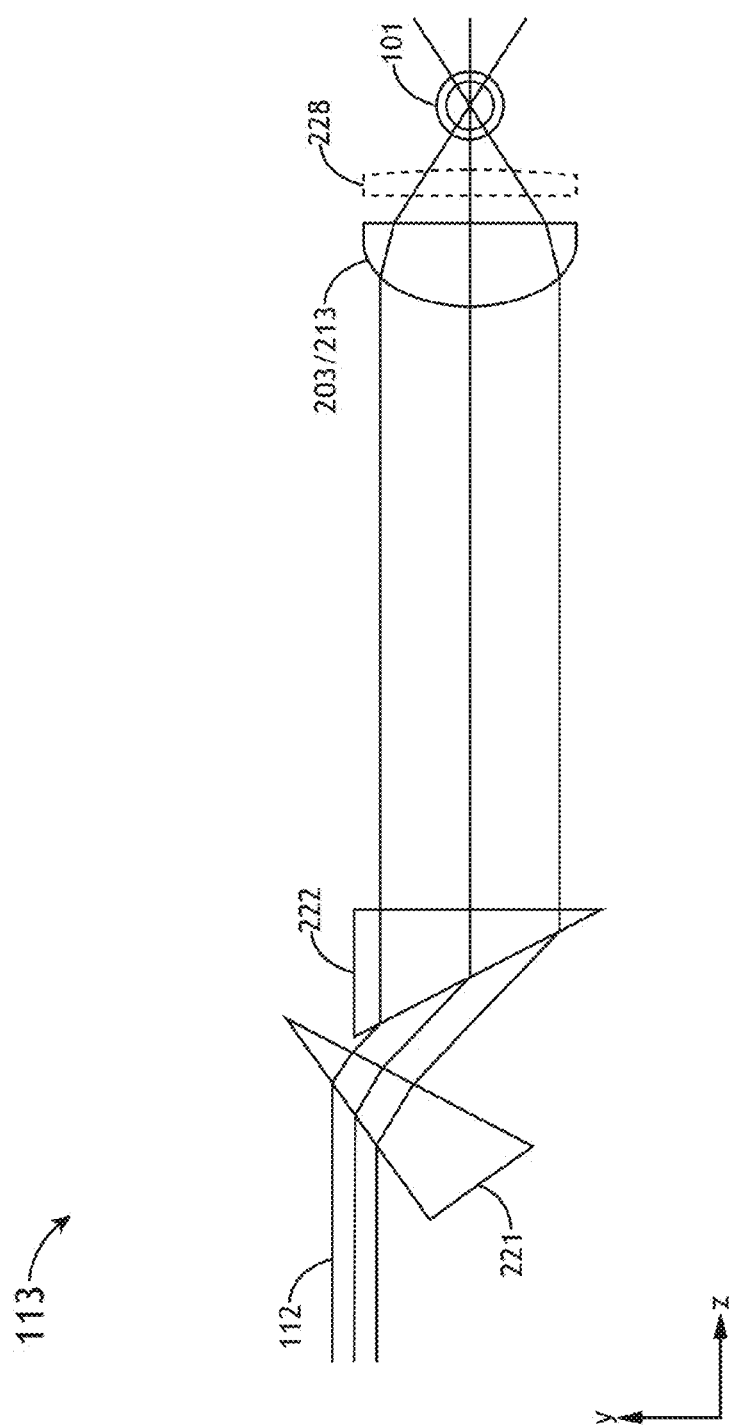

FIGS. 2A-2C illustrate schematic views of anamorphic illumination optics 113 suitable for implementation in source 100, in accordance with one or more embodiments of the present disclosure.

It is noted that the coordinate system depicted in the examples and embodiments of FIGS. 1A-1C should be interpreted to extend to FIGS. 2A-2C. In this example, the pump beam 112 is travels in the z-direction and the elliptical beam waist formed by the anamorphic illumination optics 113 is very small with high NA in the y-direction and at least 10 times larger with lower NA in the x-direction. It is noted that the scope of the present disclosure is not limited to the example ratio between the NA in the y-direction and the NA in the x-direction, which is provided above merely for illustrative purposes.

In one embodiment, as shown in FIG. 2A, the one or more anamorphic illumination optics 113 is an optical assembly including a cylindrical telescope containing two cylindrical lenses 201 and 202 in the y-direction. The cylindrical lenses 201, 202 act to expand the pump beam 112 from the pump laser 111 to a much larger size. It is noted that a cylindrical telescope may be configured so as to set collimation to compensate for most astigmatism. In another embodiment, the one or more anamorphic illumination optics 113 include an acylindrical plano-convex lens 203. For example, the acylindrical plano-convex lens 203 may have a large aperture and short focal length and may be configured to focus the beam with high NA (e.g., >0.5) to very small beam size with its waist located in or proximate to the center of the gas containment structure 101. The acylindrical lens 203 may include complex surface profile and may significantly reduce the optical aberration in the pump beam 112 so the beam size at the waist is minimized. In the x-direction, a cylindrical lens 204, with long focal length, focuses the pump beam 112 with smaller NA to a larger beam size with its waist also located in or approximately the center of the gas containment structure 101.

In another embodiment, the one or more anamorphic illumination optics 113 include one or more additional aberration compensators. For example, the one or more anamorphic illumination optics 113 may include, but are not limited to, the additional aberration compensators 208, which may be positioned before the gas containment structure 101 in order to compensate (in the x- and/or y-directions) for aberration generated by an irregular or non-perfect shape of the transmissive portion of the surface of the gas containment structure 101 (e.g., bulb) and/or aberrations from the pump laser 111 or other components. It is noted that since the NA is larger in the y-direction, correction in the y-direction is more important for image quality. As such, in one embodiment, the compensator 208 includes an acylindrical lens have one or more curved surfaces oriented in the y-z plane. The resulting elliptical beam waist in the x-y plane is shown as 117.

In another embodiment, as shown in FIG. 2B, the one or more anamorphic illumination optics 113 include an aspherical lens 213. For example, following the application of a cylindrical telescope via lenses 211 and 212, which expand the pump beam 112 to a larger size in the y-direction, the aspherical lens 213 having a large aperture and short focus may focus the beam pump 112 with high NA (>0.5) to a very small beam size with its waist located in or proximate to the center of the gas containment structure 101. It is noted that aspherical lenses are more commonly available and/or less expensive than acylindrical lenses. In another embodiment, in the x-direction, a cylindrical lens 214 with long focal length (similar to 204) may focus the pump beam 112. In another embodiment, a plano-concave cylindrical lens 215, placed in between the cylindrical lens 214 and aspherical lens 213, is configured to cancel the power generated by the aspherical lens 213 in the x-direction. In this regard, the whole lens set effectively generates an elliptical beam waist 117 similar to that depicted FIG. 2A. In another embodiment, the one or more anamorphic illumination optics 113 includes one or more additional aberration compensators. For example, one or more additional aberration compensators, such as compensator 218, may be added before the gas containment structure 101 to compensate for aberration generated in one or both directions by an irregular or imperfect shape of the transmissive portion of the gas containment structure 101 and/or aberrations from the pump laser 111 or other components.

In another embodiment, as shown in FIG. 2C, the one or more anamorphic illumination optics 113 includes two prisms configured to operate near Brewster's angle so as to expand the pump beam 112 in the y-direction. In one embodiment, prisms 221 and 222 are tuned to adjust the NA and pump beam 112 size in the y-direction without introducing any power into the system. This prism pair 221, 222 may be used as a replacement for the lenses 201, 202 in FIG. 2A (which is followed with acylindrical lens 203) or the lenses 211, 212 in FIG. 2B (which is followed with aspherical lens 213). In another embodiment, the anamorphic illumination optics 113 includes an additional aberration compensator 228. It is noted that the x-direction configuration of FIG. 2C would be the same as FIG. 2A if acylindrical lens 203 is implemented. Additionally, the x-direction configuration of FIG. 2C would be the same as FIG. 2B if aspherical lens 213 is implemented.

It is noted that the number and type of components depicted in FIGS. 2A-2C are provided merely for illustrative purposes and should not be interpreted as a limitation on the scope of the present disclosure. For example, the anamorphic illumination optics 113 of FIGS. 2A-2C may include any number and type of components known in the art of optics. For instance, instead of the cylindrical telescope implemented with two lenses (as in FIGS. 2A and 2B), an afocal telescope implemented with three lens may be used to tune the beam diameter and set focusing. In additional embodiments, one or more surfaces of the anamorphic illumination optics 113 may be coated with a selected coating to maximize the transmission of the laser pump beam 112.

Figure 3A:
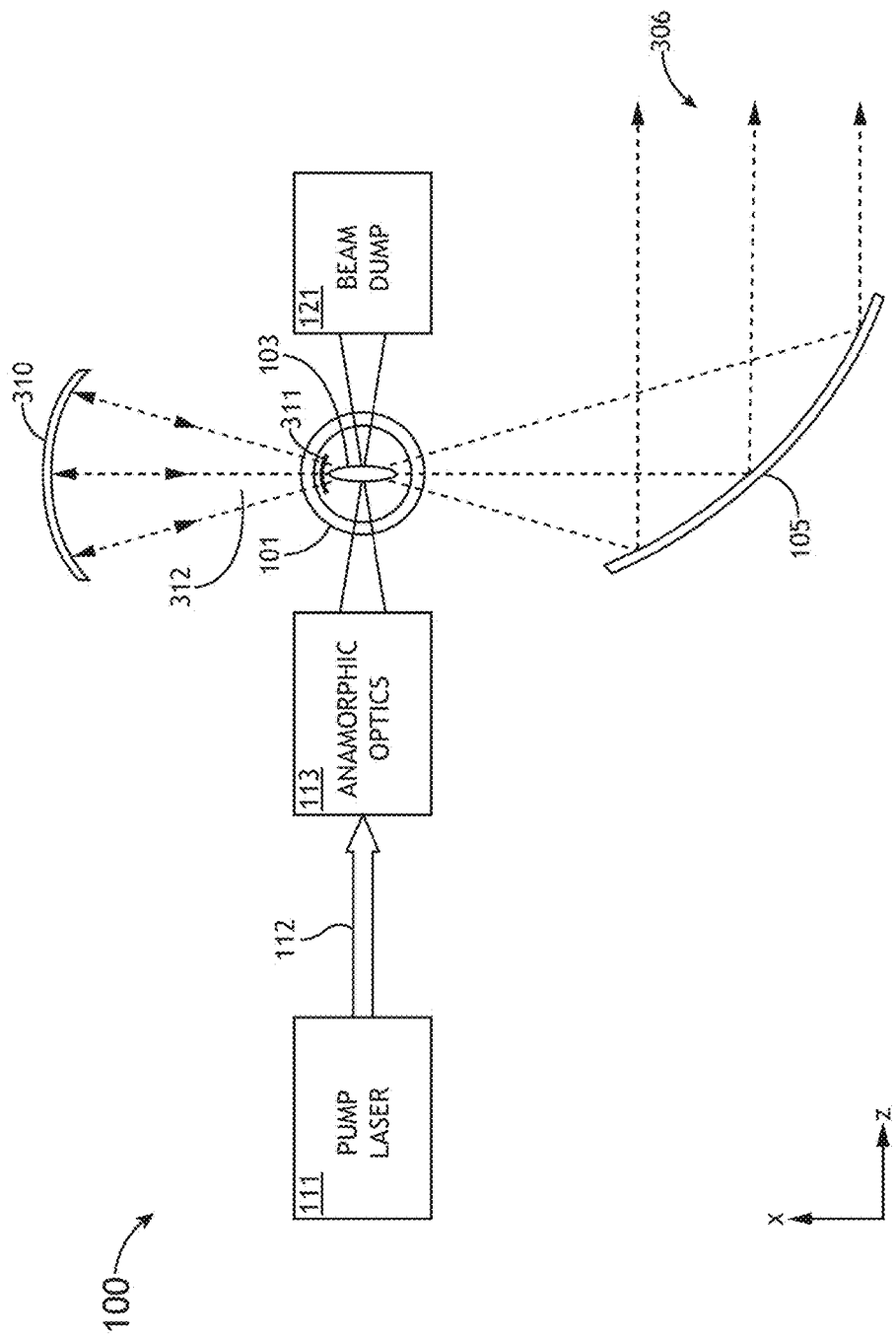
FIGS. 3A-3B illustrate the implementation of a spherical mirror inside or outside the gas containment structure of the system for generating high brightness LSP broadband radiation, in accordance with one or more embodiments of the present disclosure.
Figure 3B:
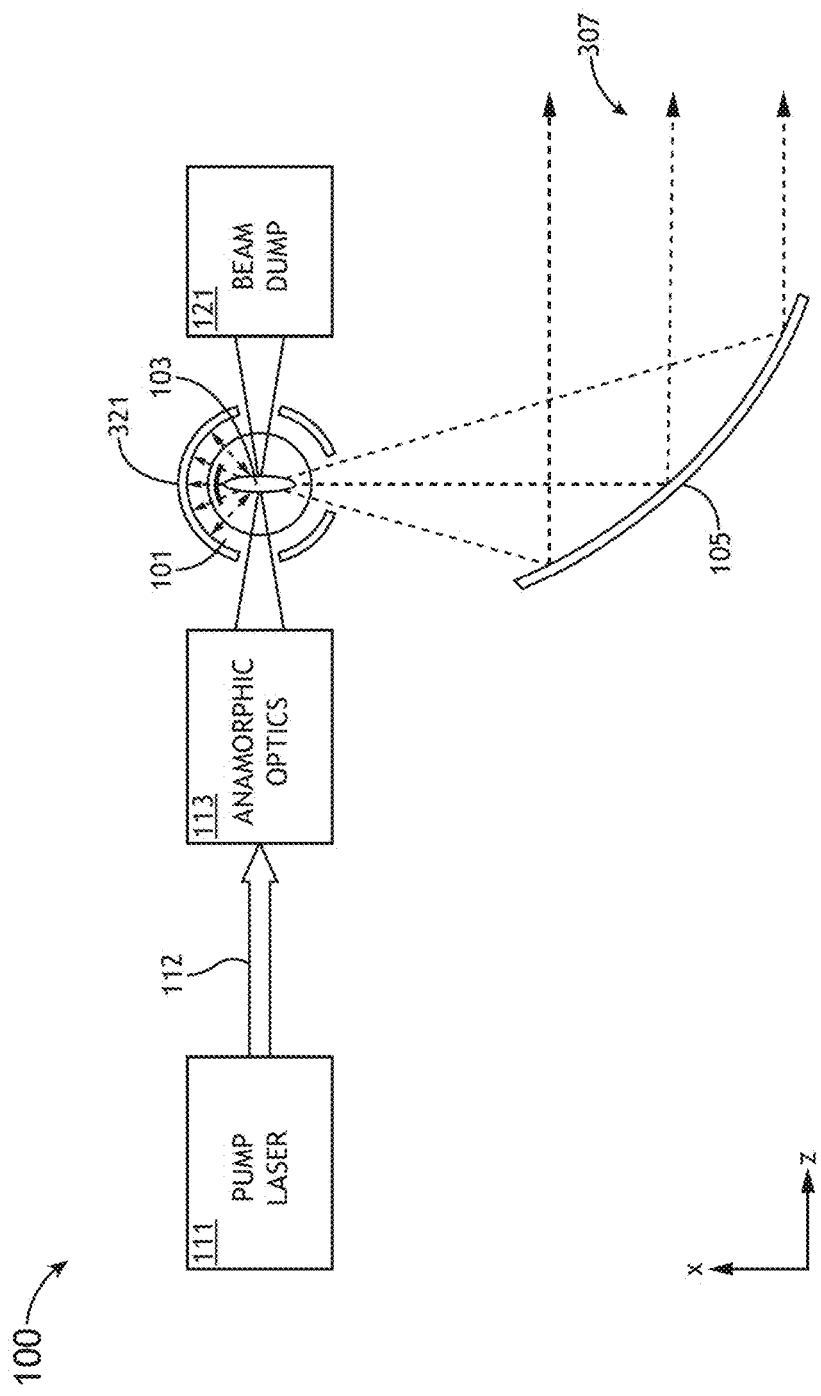

FIGS. 3A-3B illustrate the implementation of a spherical mirror inside or outside the gas containment structure 101, in accordance with one or more embodiments of the present disclosure. It is noted that, since the plasma 103 radiates in all directions, more plasma radiation may be collected within the same solid angle and with the same collection optics if the plasma radiation on the side of the gas containment structure 101 opposite from the first collection optics 105 is reflected back towards the plasma 103 and focused into the plasma 103 substantially overlapped with the beam waist of the pump beam 112.

In one embodiment, as shown in FIG. 3A, the source 100 includes an external spherical mirror 310 positioned outside of the gas containment structure 101 on the opposite side of the gas containment structure 101 from the first collection optics 105. The spherical mirror 310 may be configured to reflect the plasma radiation 312 and focus it back to the center of the plasma 103. Alternatively, the source 100 may include an internal spherical mirror 311 positioned on the inside or outside surface of the gas containment structure 101 on the opposite side of the gas containment structure 101 from the first collection optics 105. The internal spherical mirror 311 may also be configured to reflect the plasma radiation 312 and focus it back to the center of the plasma 103.

In one embodiment, the reflectors 310, 311 may comprise a broadband high-reflection coating on the outer surface or the inner surface of the transmissive portion (e.g., bulb) of the gas containment structure 101. In one embodiment, some of the reflected plasma radiation 312 may be absorbed by the plasma 103 causing the plasma 103 temperature to increase and the brightness to be enhanced. Further, the rest of the reflected radiance may pass through the plasma 103 and follow the beam path towards the first collection optics 105, where it is collected and directed to downstream optical elements. In this regard, the total collected broadband beam 306 includes three parts: 1) radiation that is initially emitted from the plasma 103 towards the first collection optics 105; 2) radiation that is reflected by reflectors 310 or 311 towards the first collection optics 105 and is enhanced by reabsorption of the reflected plasma radiation 312; and 3) radiation that is reflected by reflectors 310 or 311 towards the first collection optics 105 and is transmitted through the plasma 103.

In another embodiment, as shown in FIG. 3B, the reflector 310 or 311 may be extended in area. In one embodiment, the reflector may be as large as a full reflecting enclosure 321 (or some portion of the enclosure) with apertures to pass the incoming pump beam 112, the leftover pump beam, and the plasma radiation 312 to be collected. In another embodiment, the enclosure 321 may include multiple separate mirrors positioned outside or inside of the gas containment structure 101. In an alternative embodiment, the enclosure 321 may include reflective coatings on the outer or inner surface of the transmissive portion of the gas containment structure 101. In this example, the plasma radiation 312 may be reflected back to the plasma 103 and focused at a location that is substantially overlapped with the beam waist of the pump beam 112 and may be reabsorbed by the plasma 103. In this regard, the amount of broadband radiation emitted by the plasma 103 is enhanced as is the collection amount of broadband radiation 307. Further, the enclosure 321 may also aid in reducing the amount of light scattered into an optical system (e.g., inspection system or metrology system) incorporating the LSP source 100 as a light source.

Figure 4A:
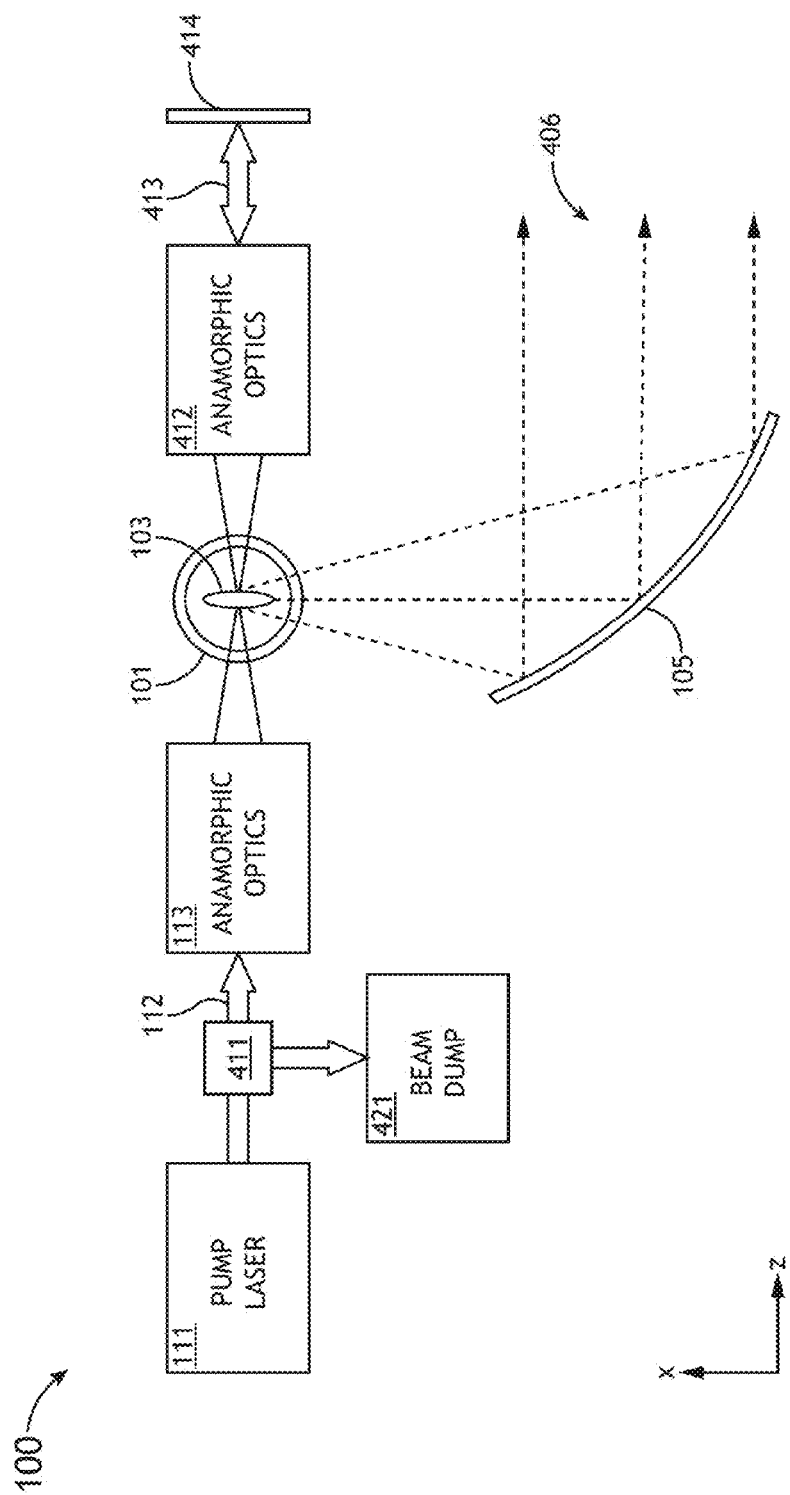
FIG. 4A illustrates the system for generating high brightness LSP broadband radiation configured for focusing unabsorbed pump laser radiation back into the plasma, in accordance with one or more embodiments of the present disclosure.

FIG. 4A illustrates source 100 configured for focusing unabsorbed pump laser radiation back into the plasma 103 substantially overlapped with the beam waist of the pump beam 112 to further pump the plasma 103, in accordance with one or more embodiments of the present disclosure. In one embodiment, the source 100 includes an optical isolator 411 positioned in the beam path so to pass the pump beam 112 out from the pump laser 111, but redirect any back-reflected beam to a beam dump 421. In another embodiment, the source 100 includes an additional set of anamorphic illumination optics 412. The anamorphic illumination optics 412 may be configured to collimate the transmitted pump beam 112 in two directions separately. For example, the anamorphic illumination optics 412 may include, but are not limited to, any optical configuration depicted in FIG. 2A, 2B, or 2C. In another embodiment, the source 100 may include one or more aberration compensators. In another embodiment, the collimated beam 413 may be reflected back by a flat mirror 414 and then focused back to the center of the plasma 103 with the anamorphic illumination optics 412. It is noted that the initial plasma absorption of the pump laser 111 may be less than 70%. As such, utilizing the unabsorbed pump power in the first pass of the pump beam 112 may greatly increase the pumping efficiency of the pump laser 111.

It is noted that the configuration depicted in FIG. 4A should not be interpreted as a limitation on the scope of the present disclosure and is provided merely for illustrative purposes. For example, the anamorphic illumination optics 412 and flat mirror 414 may be replaced by a spherical mirror positioned such that the center of curvature of the spherical mirror is coincident with the center of the plasma 103. In this manner, the focused pump beam 112 may be reflected as an inverted image back to the same location. Although a single spherical mirror may introduce some aberrations in the reflected pump beam 112 image, the plasma 103 temperature may be enhanced because additional power is absorbed from the reflected pump image.

Figure 4B:
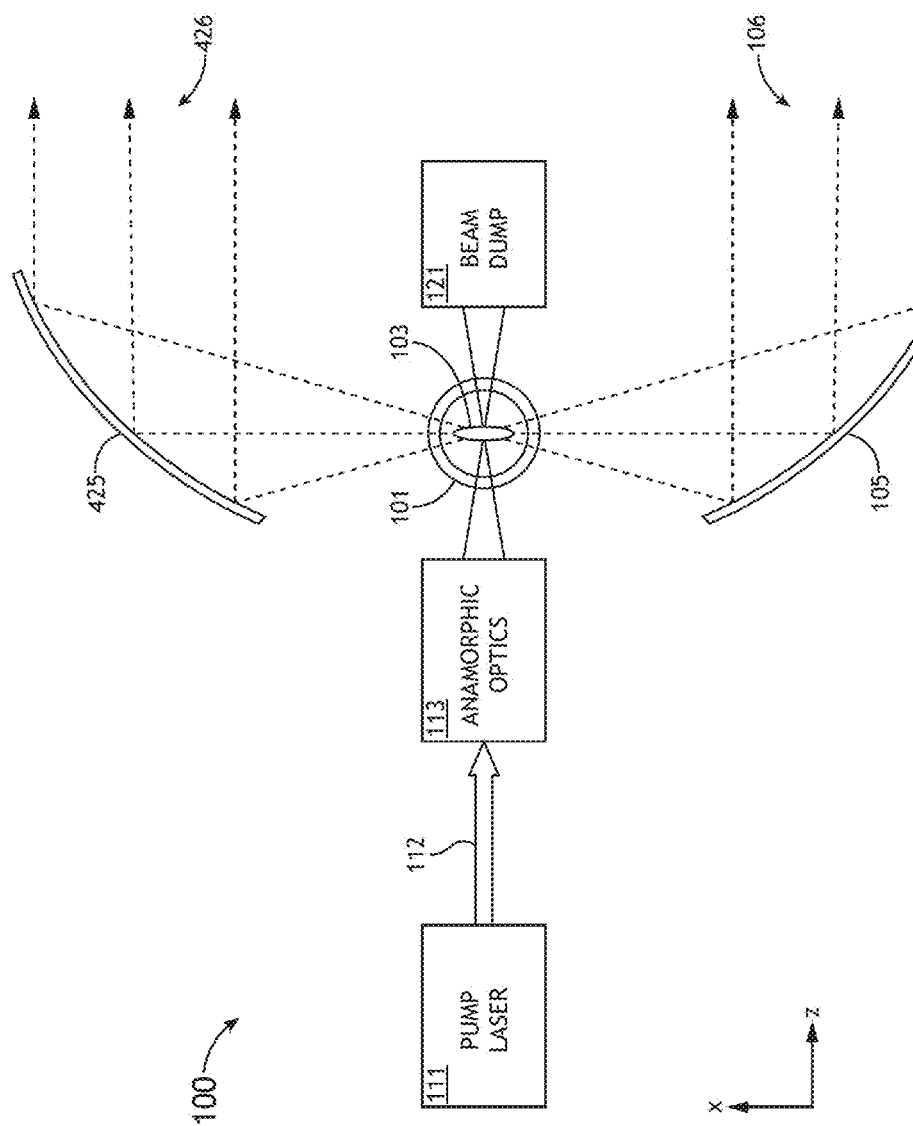
FIG. 4B illustrates the system for generating high brightness LSP broadband radiation equipped with dual channel output, in accordance with one or more embodiments of the present disclosure.

FIG. 4B illustrates the source 100 equipped with dual channel output, in accordance with one or more embodiments of the present disclosure. In one embodiment, the source 100 includes a second set of collection optics 425 configured to collect plasma radiation radiated on the opposite side of the gas containment structure 101 from the first collection optics 105. For example, the second collection optics 425 may be mirror symmetric to the first collection optics 105 along the optical axis of the pump beam 112, whereby the optical axis of the pump beam 112 is oriented along the elongated direction of the plasma 103. In this regard, the second set of collection optics 425 generates another broadband beam 426 with approximately the same intensity as the original broadband beam 106. Such a configuration may be highly advantageous for metrology or inspection systems with multiple illumination channels in that the overall usable light intensity may be enhanced and throughput may be improved. It is noted that the configuration depicted in FIG. 4A should not be interpreted as a limitation on the scope of the present disclosure and is provided merely for illustrative purposes.

It is noted that the various embodiments depicted in FIGS. 3A-4B may be combined in order to achieve enhance the overall effectiveness of the source 100 and the brightness of the plasma output.

The source 100 of the present disclosure may be implemented as the broadband illumination source in any optical system known in the art. For example, source 100 may be implemented as a broadband source for any inspection tool or metrology tool known in the art of semiconductor wafer characterization.

Figure 5:
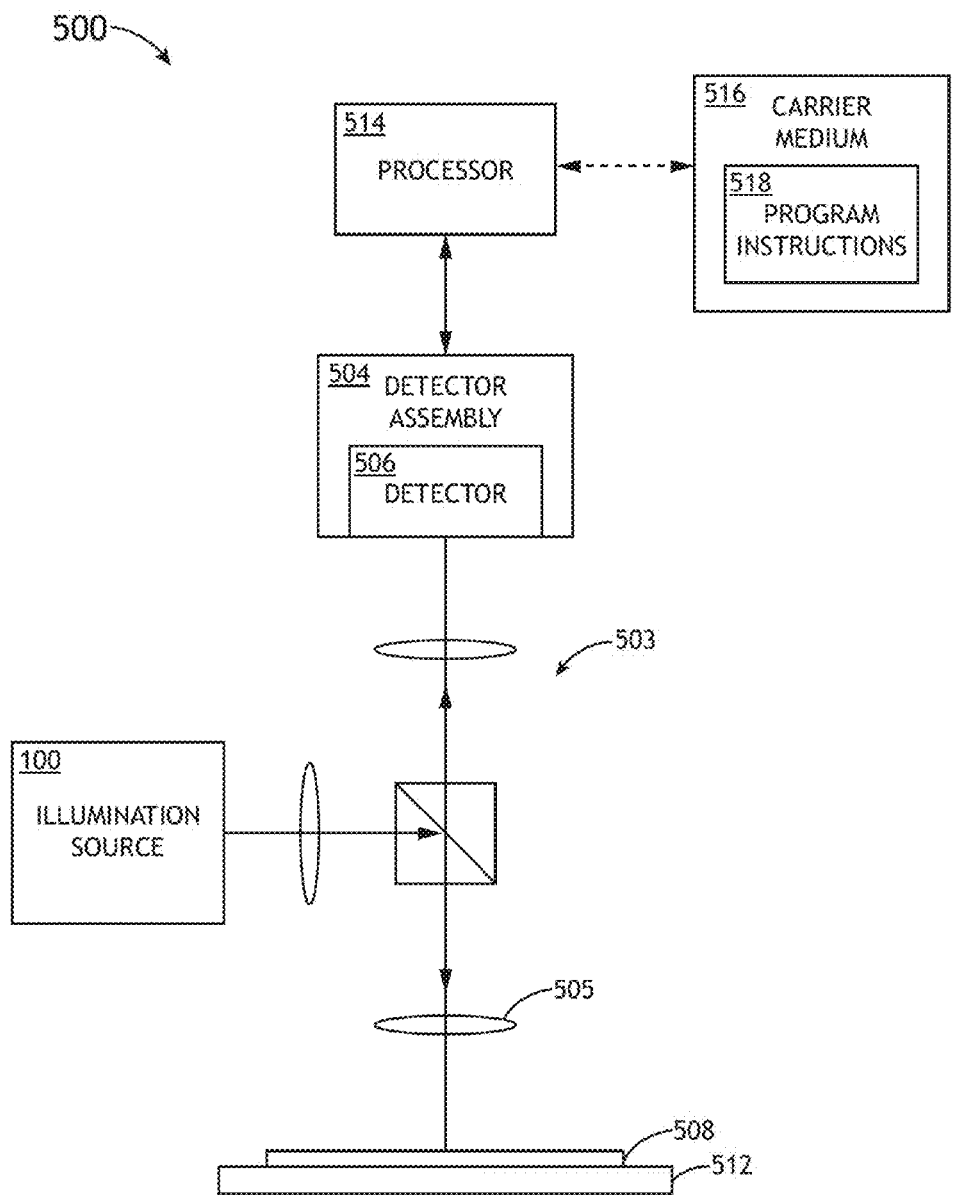
FIG. 5 illustrates a simplified schematic view of an inspection and/or metrology system implementing the system for generating high brightness LSP broadband radiation as an illumination source, in accordance with one or more embodiments of the present disclosure.

FIG. 5 illustrates a simplified schematic view of an inspection system 500 implementing broadband source 100, in accordance with one or more embodiments of the present disclosure. It is noted that, while system 500 is described in the context of sample inspection, system 500 may be extended to other optical characterization contexts, such as, imaging-based metrology. In one embodiment, the inspection system 500 is configured to inspect or measure a sample 508 (e.g., a wafer, reticle, photomask, or the like). For example, the sample 508 may be placed on a stage 512 in order to facilitate movement of different regions of the sample 508 underneath the optics. By way of another example, the stage 512 may include a linear stage (e.g., X-Y stage) or a rotation stage (e.g., R-θ stage). In an additional embodiment, the stage 512 may adjust the height of the sample 508 during inspection or measurement to maintain focus. In another embodiment, the inspection system includes an objective lens 505. For example, the objective lens 505 may be adjusted to maintain focus.

In one embodiment, the LSP broadband radiation source 100 described previously herein is implemented as the illumination source 100 of system 500. For example, the illumination source 100 may emit visible, ultraviolet (UV), deep ultraviolet (DUV) and/or vacuum ultraviolet (VUV) radiation. In one embodiment, the system 500 includes a set of optics 503 configured to direct and/or focus light from the illumination source 100 onto the surface of the sample 508. For example, the set of optics 503 may include, but are not limited to, an objective lens 505 for focusing light onto the surface of the sample 508. In another embodiment, the set of optics 503 may include one or more additional optical components (e.g., lenses or mirrors) for collecting light reflected or scattered from sample 508. The set of optics 503 may then direct the collected light from the surface of the sample 508 to the detector 506 of the detector assembly 504. The set of optics 503 may include any number and type of optics known in the art for illuminating the surface sample 508 and collecting light from the surface of the sample 508, such as, but not limited to, mirrors, lenses, and/or beam splitters.

The detector 506 of detector assembly 504 may include any light detector known in the art, such as, but not limited to, a CCD detector, a TDI-CCD detector or the like. For example, the detector 506 may include, but is not limited to, a two-dimensional array sensor or a one-dimensional line sensor. In another embodiment, the output of detector 506 is provided to one or more processors 514, which analyze the output of the detector 506. For example, the processor 514 may be configured by program instructions 518, which may be stored on a carrier medium 516 (e.g., memory).

In one embodiment, the system 500 illuminates a line on sample 508, and, in response, the detector 506 collects scattered and/or reflected light in one or more dark-field and/or bright-field collection channels. In this regard, the detector 506 may include a line sensor or an electron-bombarded line sensor. In another embodiment, the system 500 illuminates multiple spots on sample 508, and, in response, the detector 506 collects scattered and/or reflected light in one or more dark-field and/or bright-field collection channels. In this regard, the detector 506 may include a two-dimensional array sensor or an electron-bombarded two-dimensional array sensor.

Details related to wafer inspection or metrology are described in U.S. patent application Ser. No. 13/554,954 to Romanovsky et al., filed on Jul. 9, 2012; U.S. Pat. No. 7,957,066 to Armstrong et al., issued on Jun. 7, 2011; U.S. Pat. No. 7,345,825 to Chuang et al., issued on Mar. 18, 2008; U.S. Pat. No. 5,999,310 to Shafer et al., issued on Dec. 7, 1999; and U.S. Pat. No. 7,525,649 to Leong et al., issued on Apr. 28, 2009, which are each incorporated herein by reference in their entirety.

Figure 6:
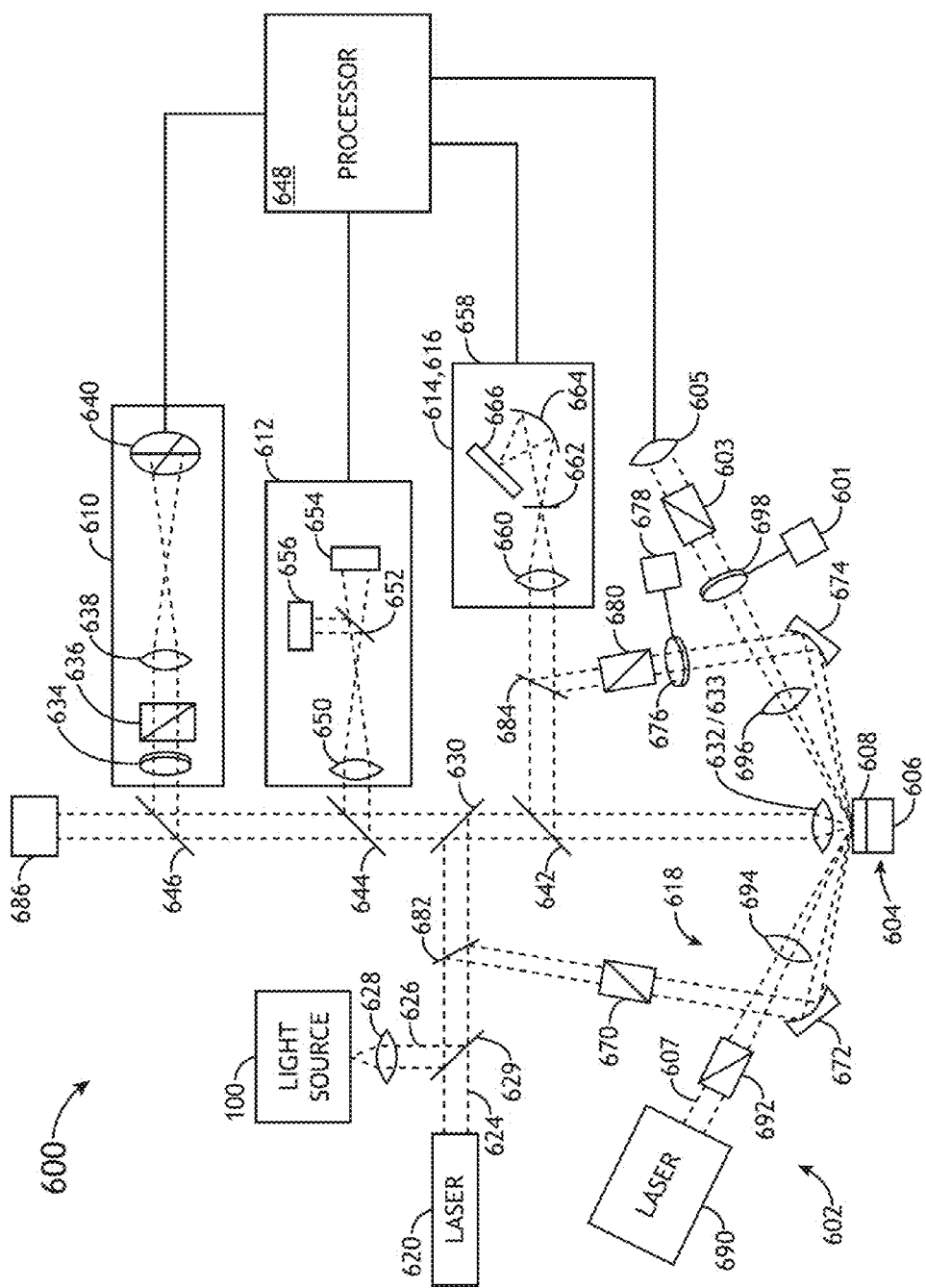
FIG. 6 illustrates a simplified schematic view of a metrology system configured to implementing the system for generating high brightness LSP broadband radiation as an illumination source, in accordance with one or more embodiments of the present disclosure.

FIG. 6 illustrates a simplified schematic view of a metrology system 600 implementing broadband radiation source 100, in accordance with one or more embodiments of the present disclosure.

In one embodiment, the metrology system 600 is configured with up to six different non-contact optical measurement sub-systems and may incorporate the LSP broadband radiation source 100, as described previously herein. For example, the metrology system 600 may include a Beam Profile Ellipsometer (BPE) 610, a Beam Profile Reflectometer (BPR) 612, a Broadband Reflective Spectrometer (BRS) 614, a Deep Ultra Violet Reflective Spectrometer (DUV) 616, a Broadband Spectroscopic Ellipsometer (BSE) 618, and a reference ellipsometer 602. These six optical measurement devices may utilize as few as three optical sources: lasers 620 and 690, and broadband source 100. By way of another example, the laser 620 may generate a probe beam 624 and the broadband source 100 may generate a probe beam 626 (which is collimated by lens 628 and directed along the same path as the probe beam 624 by a mirror 629). For example, the laser 620 may be, but is not limited to, a solid state laser diode which emits a linearly polarized 3 mW beam at a visible or near IR wavelength such as a wavelength near 670 nm. As noted above, the broadband source 100 may include the broadband LSP source described previously herein. For example, the broadband source 100 may produce a polychromatic beam that covers a spectrum of 200 nm to 800 nm or broader.

In one embodiment, the metrology system 600 includes probe beams 624, 626. For example, the probe beams 624, 626 may be reflected by a mirror 630, and pass through a mirror 642 to a sample 604. By way of another example, the probe beams 624, 626 may be focused onto the surface of the sample 604 with a lens 632 or lens 633. For instance, the two lenses 632, 633 may be mounted in a turret (not shown) and may be alternatively movable into the path of the probe beams 624, 626. Further, the lens 632 may be a spherical, microscope objective lens with a high numerical aperture (on the order of 0.90 NA) to create a large spread of angles of incidence with respect to the sample surface and to create a spot size of about one micron in diameter. The lens 633 may be a reflective lens having a lower numerical aperture (on the order of 0.4 NA) and capable of focusing deep UV light to a spot size of about 10-15 microns.

In another embodiment, the beam profile ellipsometry (BPE) 610 includes a quarter wave plate 634, a polarizer 636, lens 638, and a quad detector 640. In operation, linearly polarized probe beam 624 may be focused onto the sample 604 by the lens 632. For example, light reflected from the sample surface may pass up through the lens 632, through the mirrors 642, 630, and 644, and directed into the BPE 610 by the mirror 646. The positions of the rays within the reflected probe beam may correspond to specific angles of incidence with respect to the surface of the sample. In another embodiment, the quarter-wave plate 634 may retard the phase of one of the polarization states of the beam by 90 degrees. Further, the linear polarizer 636 may cause the two polarization states of the beam to interfere with each other. For maximum signal, the axis of the polarizer 636 may be oriented at an angle of 45 degrees with respect to the fast and slow axis of the quarter-wave plate 634. The quad detector 640 may be a quad-cell detector with four radially disposed quadrants that each intercept one quarter of the probe beam and generate a separate output signal proportional to the power of the portion of the probe beam striking that quadrant. The output signals from each quadrant may be sent to a processor 648. It is noted that, by monitoring the change in the polarization state of the beam, ellipsometric information, such as $\psi$ and $\Delta$, can be determined. To determine this information, the processor 648 takes the difference between the sums of the output signals of diametrically opposed quadrants, a value which varies linearly with film thickness for very thin films. Beam profile ellipsometry is discussed in U.S. Pat. No. 5,181,080 to Fanton et al., issued on Jan. 19, 1993, which is incorporated herein by reference in the entirety.

In another embodiment, the BPR 612 includes lens 650, a beam splitter 652 and two linear detector arrays 654 and 656 to measure the reflectance of the sample. In operation, the linearly polarized probe beam 624 may be focused onto the sample 604 by the lens 632, with various rays within the beam striking the sample surface at a range of angles of incidence. Light reflected from the sample surface may pass up through the lens 632, through the mirrors 642 and 630, and directed into the BPR 612 by the mirror 644. The positions of the rays within the reflected probe beam may correspond to specific angles of incidence with respect to the surface of the sample. The lens 650 may spatially spread the beam two-dimensionally. The beam splitter 652 may separate the S and P components of the beam, and detector arrays 654 and 656 may be oriented orthogonal to each other to isolate information about S and P polarized light. The higher angles of incidence rays may fall closer to the opposed ends of the arrays. The output from each element in the diode arrays may correspond to different angles of incidence. The detector arrays 654, 656 may measure the intensity across the reflected probe beam as a function of the angle of incidence with respect to the sample surface. The processor 648 may receive the output of the detector arrays 654, 656, and derive the thickness and/or refractive index of the thin film layer 608 based on these angular dependent intensity measurements by utilizing various types of modeling algorithms. For example, optimization routines which use iterative processes such as least square fitting routines may be employed. One example of this type of optimization routine is described in "Multiparameter Measurements of Thin Films Using Beam-Profile Reflectivity," by Fanton, et al., Journal of Applied Physics, Vol. 73, No. 11, p. 7035, 1993, which is incorporated herein by reference in the entirety.

Another example appears in "Simultaneous Measurement of Six Layers in a Silicon on Insulator Film Stack Using Spectrophotometry and Beam Profile Reflectometry," by Leng, et al., Journal of Applied Physics, Vol. 81, No. 8, page 3570, 1997, which is incorporated herein by reference in the entirety. Beam profile reflectometry (BPR) is discussed in U.S. Pat. No. 4,999,014 to Gold et al., issued on Mar. 12, 1991, which is incorporated herein by reference in the entirety.

In another embodiment, the BRS 614 simultaneously probes the sample 604 with multiple wavelengths of light. In one embodiment, BRS 14 uses lens 632 and includes a broadband spectrometer 658. The broadband spectrometer 658 may include any broadband spectrometer known in the art. In one embodiment, the spectrometer 658 may include lens 660, an aperture 662, a dispersive element 664 and a detector array 666. During operation, the probe beam 626 from the broadband source 100 may be focused onto the sample 604 by the lens 632. Light reflected from the surface of the sample may pass up through the lens 632, and may be directed by the mirror 642 (through the mirror 684) to the spectrometer 658. The lens 660 may focus the probe beam through the aperture 662, which may define a spot in the field of view on the sample surface to analyze. The dispersive element 664, such as a diffraction grating, prism or holographic plate, may angularly disperse the beam as a function of wavelength to individual detector elements contained in the detector array 666. The different detector elements may measure the optical intensities of the different wavelengths of light contained in the probe beam. For instance, the different detector elements may measure the optical intensities of the different wavelengths of light simultaneously. In another embodiment, the detector array 666 may be a charge-coupled device (CCD) camera, or a photomultiplier with suitably dispersive or otherwise wavelength selective optics. It is noted that a monochromator could be used to serially measure the different wavelengths (one wavelength at a time) using a single detector element. Further, the dispersive element 664 may also be configured to disperse the light as a function of wavelength in one direction, and as a function of the angle of incidence with respect to the sample surface in an orthogonal direction so that simultaneous measurements as a function of both wavelength and angle of incidence are possible. The processor 648 may process the intensity information measured by the detector array 666. The BRS 614 may simultaneously probe the sample 604 with multiple wavelengths of light.

In another embodiment, the DUV 616 uses the same spectrometer 658 to analyze the probe beam 626 as the BRS 614, except that the DUV 616 uses the reflective lens 633 instead of the focusing lens 632. To operate the DUV 616, the turret containing the lenses 632, 633 may be rotated so that the reflective lens 633 may be aligned in the probe beam 626. In some embodiments, the reflective lens 633 may be necessary because solid objective lenses cannot sufficiently focus the UV light onto the sample.

In another embodiment, the BSE 618 includes a polarizer 670, focusing mirror 672, collimating mirror 674, rotating compensator 676, and analyzer 680. In operation, mirror 682 may direct at least part of probe beam 626 to the polarizer 670, which creates a known polarization state for the probe beam, preferably a linear polarization. The focusing mirror 672 may focus the beam onto the sample surface at an oblique angle (e.g., on the order of 70 degrees to the normal of the sample surface). It is noted that the reflected beam may generally have a mixed linear and circular polarization state after interacting with the sample, based upon the composition and thickness of the sample's film 608 and substrate 606. The reflected beam may be collimated by the collimating mirror 674, which directs the beam to the rotating compensator 676. The rotating compensator 676 may introduce a relative phase delay δ (phase retardation) between a pair of mutually orthogonal polarized optical beam components. The rotating compensator 676 may be rotated at an angular velocity ω about an axis substantially parallel to the propagation direction of the beam, preferably by an electric motor 678. The analyzer 680 (e.g., another linear polarizer) may mix the polarization states incident on it. By measuring the light transmitted by the analyzer 680, the polarization state of the reflected probe beam may be determined. The mirror 684 may direct the beam to the spectrometer 658, which simultaneously measures the intensities of the different wavelengths of light in the reflected probe beam that pass through the compensator/analyzer combination. The processor 648 may receive the output of the detector 666, and process the intensity information measured by the detector 666 as a function of wavelength and as a function of the azimuth (rotational) angle of the rotating compensator 676 about its axis of rotation, to solve for sample characteristics, such as the ellipsometric values ψ and Δ. Broadband spectroscopic ellipsometry is described in U.S. Pat. No. 5,877,859, to Aspnes et al., issued on Mar. 2, 1999, which is incorporated herein by reference in the entirety.

In another embodiment, the detector/camera 686 is positioned above the mirror 646, and can be used to view beams reflected off of the sample 64 for alignment and focus purposes.

In another embodiment, in order to calibrate the BPE 610, the BPR 612, the BRS 614, the DUV 616, and/or the BSE 618, the metrology system 600 includes the wavelength stable calibration reference ellipsometer 602 used in conjunction with a reference sample 604. For example, the ellipsometer 602 may include a light source 690, polarizer 692, lenses 694, 696, rotating compensator 698, analyzer 603 and detector 605.

In one embodiment, the light source 690 (e.g., one or more lasers) produces a quasi-monochromatic probe beam 607 having a known stable wavelength and stable intensity. For example, the wavelength of beam 607, which is a known constant or a measured value, may be provided to the processor 648 so that the ellipsometer 602 can accurately calibrate the optical measurement devices in the system 600. In another embodiment, the beam 607 interacts with a polarizer 692 to create a known polarization state. For example, the polarizer 692 may be, but is not limited to, a linear polarizer comprising a quartz Rochon prism. It is noted that the polarization is not limited to linear polarization or even complete polarization. By way of another example, the polarizer 692 may also be made from calcite.

The azimuth angle of the polarizer 692 may be oriented so that the plane of the electric vector associated with the linearly polarized beam exiting from the polarizer 692 is at a known angle with respect to the plane of incidence (defined by the propagation direction of the beam 607 and the normal to the surface of sample 64). The azimuth angle is preferably selected to be on the order of 30 degrees because the sensitivity is optimized when the reflected intensities of the P and S polarized components are approximately balanced. It is noted that the polarizer 692 may be omitted if the light source 690 emits light with the desired known polarization state.

In another embodiment, the beam 607 is focused onto the sample 604 by lens 694 at an oblique angle. For example, the beam 607 may impinge the sample 604 at an angle on the order of 70 degrees to the normal of the sample surface because sensitivity to sample properties is maximized in the vicinity of the Brewster or pseudo-Brewster angle of a material. Based upon ellipsometric principles, the reflected beam may generally have a mixed linear and circular polarization state after interacting with the sample, as compared to the linear polarization state of the incoming beam. The lens 696 may collimate the beam 607 after its reflection off of the sample 604.

In another embodiment, the beam 607 then passes through the rotating compensator (retarder) 698, which introduces a relative phase delay $\delta_r$ (phase retardation) between a pair of mutually orthogonal polarized optical beam components. The amount of phase retardation may be a function of the wavelength, the dispersion characteristics of the material used to form the compensator, and/or the thickness of the compensator. For example, the compensator 698 may be rotated at an angular velocity $\omega_r$ about an axis substantially parallel to the propagation direction of the beam 607 (e.g., rotated by an electric motor 601). The compensator 698 may be any wave-plate compensator known in the art (e.g., a crystal quartz). The thickness and material of the compensator 698 may be selected such that a desired phase retardation of the beam is induced. In one embodiment, the compensator 698 may be a bi-plate compensator constructed of two parallel plates of anisotropic material (e.g., birefringent material), such as quartz crystals of opposite handedness, where the fast axes of the two plates are perpendicular to each other and the thicknesses are nearly equal, differing enough to realize a net first-order retardation for the wavelength produced by the light source 690.

In another embodiment, the beam 607 then interacts with analyzer 603, which serves to mix the polarization states incident on it. For example, the analyzer 603 may be another linear polarizer, preferably oriented at an azimuth angle of 45 degrees relative to the plane of incidence. However, any optical device that serves to appropriately mix the incoming polarization states may be used as an analyzer. The analyzer 603 may be a quartz Rochon or Wollaston prism.

It is noted that the compensator 698 can be located either between the sample 604 and the analyzer 603 (as shown in FIG. 6), or between the sample 604 and the polarizer 692. It is further noted that the polarizer 670, the lenses 694, 696, the compensator 698 and the polarizer 603 may be all optimized in their construction for the specific wavelength of light produced by the light source 690, which maximizes the accuracy of the ellipsometer 602.

In another embodiment, the beam 607 then enters detector 605, which measures the intensity of the beam passing through the compensator/analyzer combination. For example, the processor 648 may process the intensity information measured by the detector 605 to determine the polarization state of the light after interacting with the analyzer, and therefore the ellipsometric parameters of the sample. This information processing may include measuring beam intensity as a function of the azimuth (rotational) angle of the compensator about its axis of rotation. This measurement of intensity as a function of compensator rotational angle may be effectively a measurement of the intensity of beam 607 as a function of time, since the compensator angular velocity is usually known and a constant.

It is noted that the output of light source 690 can also be used to calibrate the wavelength measurements made by the spectrometer 658. The sample 64 can be tipped, or replaced by a tipped mirror, to direct the beam 607 up to the mirror 642 and to the dispersion element 664. By knowing the exact wavelength of light produced by the light source 690, the processor 648 can calibrate the output of the detector 66 by determining which pixel(s) corresponds to that wavelength of light.

It is noted that the calibrating ellipsometer 602 of the present disclosure is not limited to the specific rotating compensator ellipsometer configuration discussed above, which is provided merely for illustrative purposes. It is further noted that the scope of the present disclosure may extend to any ellipsometer configuration in conjunction with the light source 690 (having a known wavelength) that measures the polarization state of the beam after interaction with the sample and provides the necessary information about the sample 604 for calibrating non-contact optical measurement devices. For example, another ellipsometric configuration may involve rotating polarizer 692 or analyzer 603 with motor 601, instead of rotating the compensator 698.

A metrology system is described in U.S. Pat. No. 6,297,880 to Rosencwaig, issued on Oct. 2, 2001, which is incorporated herein by reference in the entirety. Scatterometry measurements performed with a metrology system are described in U.S. Pat. No. 6,429,943 to Opsal et al., issued on Aug. 6, 2002, which is incorporated herein by reference in the entirety. A metrology system incorporating a spectroscopic ellipsometer and a spectrophotometer is described in U.S. Pat. No. 5,608,526 to Piwonka-Corle et al., issued on Mar. 4, 1997, which is incorporated herein by reference in the entirety.

Figure 7:
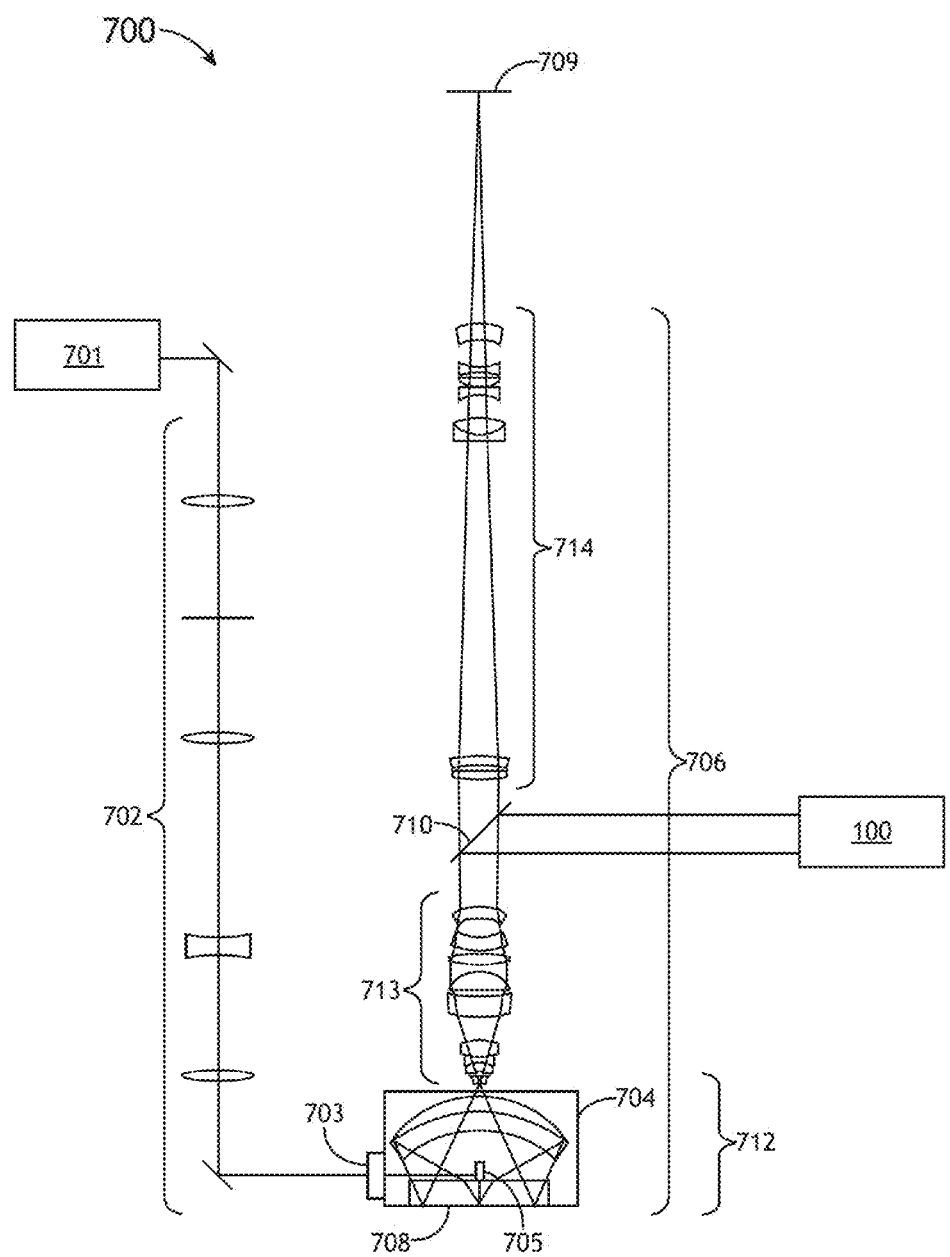
FIG. 7 illustrates a simplified schematic view of a catadioptric imaging system implementing the system for generating high brightness LSP broadband radiation as an illumination source, in accordance with one or more embodiments of the present disclosure.

FIG. 7 illustrates simplified schematic view of catadioptric imaging system 700 implementing the broadband source 100, in accordance with one or more embodiments of the present disclosure.

The catadioptric imaging system 700 may be configured as an inspection system. In one embodiment, the system 700 include a bright-field inspection mode and an, optional, dark-field inspection mode. In another embodiment, the system 700 incorporates a laser 701 and the broadband source 100, as described previously herein.

In one embodiment, in an optional dark-field mode, the adaptation optics 702 control the laser illumination beam size and profile on the surface being inspected. In another embodiment, the catadioptric imaging system 700 includes a mechanical housing 704. For example, the mechanical housing 704 may include an aperture, a window 703, and a prism 705 to redirect the laser along the optical axis at normal incidence to the surface of a sample 708. In another embodiment, the prism 705 directs the specular reflection from surface features of the sample 708 out of objective 706. For example, the objective 706 may collect light scattered by the sample 708 and focus it onto sensor 709. Further, the lenses of the objective 706 can be provided in the general form of a catadioptric objective 712, a focusing lens group 713, and a tube lens section 714, which may, optionally, include zoom capability. Laser 701 may incorporate bandwidth control as described herein.

In another embodiment, in a bright-field mode, the broadband source 100 may direct broadband light to beam a splitter 710, which reflects that light towards focusing lens group 713 and the catadioptric objective 712. For example, the catadioptric objective 712 may illuminate the sample 708 with the broadband light. Light that is reflected or scattered from the sample may be collected by the objective 706 and focused on the sensor 709. In another embodiment, the broadband source 100 may also include an auto-focus system to provide a signal to control the height of sample 708 relative to the catadioptric objective 712. A catadioptric imaging system is described in U.S. Pat. No. 7,345,825, issued on Mar. 18, 2008, which is incorporated herein by reference in the entirety.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A high brightness laser-sustained plasma broadband light source comprising:
   a gas containment structure;
   a pump laser configured to generate a pump beam including illumination of a wavelength at least proximate to a weak absorption line of a neutral gas contained in the gas containment structure;
   one or more anamorphic illumination optics configured to focus the pump beam into an approximately elliptical beam waist positioned in or proximate to the center of the gas containment structure; and
   one or more first collection optics configured to collect broadband radiation emitted by the plasma in a direction substantially aligned with a longer axis of the elliptical beam waist.

2. The light source of claim 1, further comprising:
   a plasma ignition device.

3. The light source of claim 2, wherein the plasma ignition device comprises:
   at least one of a set of electrodes or a pulsed laser.

4. The light source of claim 1, wherein the gas containment structure comprises:
   at least one of a plasma bulb, a plasma cell, or a plasma chamber.

5. The light source of claim 1, wherein the gas comprises:
   at least one of an inert gas, a non-inert gas, or a mixture of two or more gases.

6. The light source of claim 5, wherein the gas comprises:
   at least one of xenon, argon, or mercury.

7. The light source of claim 1, wherein the pump laser comprises:
at least one of a fiber laser or a solid-state laser.

8. The light source of claim 1, wherein the wavelength of light of the pump beam is approximately 1070 nm.

9. The light source of claim 1, further comprising:
a second pump laser configured to generate a second pump beam including light of a wavelength not absorbed by the neutral gas, wherein the output wavelength of the second pump laser is absorbed by an ionized gas in the plasma.

10. The light source of claim 9, wherein the wavelength of light of the second pump beam is between 515 nm and 540 nm.

11. The light source of claim 1, wherein the one or more anamorphic illumination optics comprise:
at least one of an acylindrical lens or an aspheric lens.

12. The light source of claim 1, wherein the one or more anamorphic illumination optics comprise:
an aberration compensator configured to compensate for aberration caused by at least one of a shape of the gas containment structure or the pump laser.

13. The light source of claim 1, wherein the elliptical beam waist has a ratio of major axis to minor of at least 10.

14. The light source of claim 13, wherein the one or more anamorphic illumination optics are configured to focus with a numerical aperture (NA) greater than 0.5 in the direction corresponding to the shorter axis of the elliptical beam waist, and with an NA less than 0.2 in the direction corresponding to the longer axis of the elliptical beam waist.

15. The light source of claim 13, wherein the one or more anamorphic illumination optics are configured such that the minor axis of the elliptical beam waist is less than 5 μm and the major axis of the elliptical beam waist is between 50 μm and 500 μm.

16. The light source of claim 1, wherein the first set of collection optics are configured to collect the broadband radiation in a direction substantially aligned with a longer axis of the elliptical beam waist.

17. The light source of claim 1, further comprising:
a reflector placed on an opposite side of the gas containment structure from the first collection optics and configured to focus broadband radiation back to the plasma substantially overlapping the beam waist of the pump laser.

18. The light source of claim 1, further comprising:
a reflector configured to reflect and focus unabsorbed pump laser illumination to the plasma substantially overlapped with the beam waist of the pump laser.

19. The light source of claim 1, further comprising:
a second set of collection optics configured to collect illumination emitted by the plasma on an opposite side of the gas containment structure from the first set of collection optics.

20. A method to generate high brightness broadband light comprising:
providing a volume of gas in a gas containment structure;
igniting a plasma within the volume of the gas in the gas containment structure;
generating a pump laser beam including illumination having a wavelength at least proximate to a weak neutral absorption line of the gas in the gas containment structure;
shaping and focusing the pump laser beam with one or more anamorphic illumination optics to form an elliptical beam waist located at least proximate to the center of the gas containment structure; and
collecting broadband radiation emitted by the plasma in a direction substantially aligned with a longer axis of the elliptical beam waist.

21. The method of claim 20, wherein the igniting a plasma within the volume of the gas in the gas containment structure comprises:
igniting a plasma within the volume of the gas in the gas containment structure with an a.c. discharge from a set of electrodes.

22. The method of claim 20, wherein the igniting a plasma within the volume of the gas in the gas containment structure comprises:
igniting a plasma within the volume of the gas in the gas containment structure with a pulsed laser.

23. The method of claim 20, wherein the provided gas comprises:
at least one of an inert gas, a non-inert gas, or a mixture of two or more gases.

24. The method of claim 23, wherein the gas comprises:
at least one of xenon, argon, or mercury.

25. The method of claim 20, wherein the pump laser beam is generated from at least one of a fiber laser or a solid state laser.

26. The method of claim 24, wherein the wavelength of the pump beam is approximately 1070 nm.

27. The method of claim 20, further comprising:
generating a second pump laser beam having an output wavelength that is not absorbed by the neutral gas, wherein the output wavelength of the second pump laser is absorbed by an ionized gas in the plasma.

28. The method of claim 27, wherein the wavelength of light of the second pump laser beam is between 515 nm and 540 nm.

29. The method of claim 20, wherein the one or more anamorphic illumination optics comprise:
at least one of an acylindrical lens or an aspheric lens.

30. The method of claim 20, wherein the one or more anamorphic illumination optics comprise:
an aberration compensator configured to compensate for aberration caused by at least one of a shape of the gas containment structure or the pump laser.

31. The method of claim 20, wherein the elliptical beam waist has a ratio of major axis to minor of at least 10.

32. The method of claim 31, wherein the one or more anamorphic illumination optics are configured to focus with a numerical aperture (NA) greater than 0.5 in the direction corresponding to the shorter axis of the elliptical beam waist, and with an NA less than 0.2 in the direction corresponding to the longer axis of the elliptical beam waist.

33. The method of claim 32, wherein the one or more anamorphic illumination optics are configured such that the minor axis of the elliptical beam waist is less than 5 μm and the major axis of the elliptical beam waist is between 50 μm and 500 μm.

34. The method of claim 20, wherein the first set of collection optics are configured to collect the broadband radiation in a direction substantially aligned with a longer axis of the elliptical beam waist.

35. The method of claim 20, further comprising:
reflecting broadband radiation back to the plasma substantially overlapping the beam waist of the pump laser with a reflector placed on an opposite side of the gas containment structure from the first collection optics.

36. The method of claim 20, further comprising:
reflecting and focusing unabsorbed pump laser illumination to the plasma substantially overlapped with the beam waist of the pump laser.

37. The method of claim 20, further comprising:
collecting broadband radiation emitted by the plasma on an opposite side of the gas containment structure from the first collection optics with a second set of collection optics.

38. The method of claim 20, wherein the anamorphic illumination optics are further configured to create a beam profile that is flatter than a Gaussian in the direction of the major axis of the elliptical beam waist.

* * * * *